(12) United States Patent
Estes et al.

(10) Patent No.: US 9,205,192 B2
(45) Date of Patent: Dec. 8, 2015

(54) METHOD AND SYSTEM FOR MANUAL AND AUTONOMOUS CONTROL OF AN INFUSION PUMP

(75) Inventors: Mark C. Estes, Malibu, CA (US);
Mitchell Wenger, Ross, CA (US);
Morten Mernoe, Charlottenlund (DK);
James Causey, Simi Valley, CA (US)

(73) Assignee: Bigfoot Biomedical, Inc., Milpitas, CA (US)

( * ) Notice: Subject to any disclaimer, the term of this patent is extended or adjusted under 35 U.S.C. 154(b) by 422 days.

(21) Appl. No.: 13/489,603

(22) Filed: Jun. 6, 2012

(65) Prior Publication Data

US 2012/0245522 A1    Sep. 27, 2012

Related U.S. Application Data

(62) Division of application No. 13/468,669, filed on May 10, 2012, which is a division of application No. 11/557,926, filed on Nov. 8, 2006, now Pat. No. 8,192,394.

(60) Provisional application No. 60/734,398, filed on Nov. 8, 2005.

(51) Int. Cl.
*A61M 31/00* (2006.01)
*A61M 5/20* (2006.01)
*A61M 5/172* (2006.01)
*G06Q 50/22* (2012.01)
*G06F 19/00* (2011.01)
*A61M 5/145* (2006.01)
(Continued)

(52) U.S. Cl.
CPC ........... *A61M 5/172* (2013.01); *G06F 19/3468* (2013.01); *G06Q 50/22* (2013.01); *A61M 5/14566* (2013.01); *A61M 2005/14268* (2013.01); *A61M 2005/31518* (2013.01); *A61M 2205/18* (2013.01); *A61M 2205/3561* (2013.01); *A61M 2205/3592* (2013.01)

(58) Field of Classification Search
CPC ........... G06F 19/3468; G06F 19/3475; A61M 5/14244; A61M 2005/14208; A61M 5/1723; A61M 2205/6054; A61M 2205/6072
USPC ............................... 604/151, 65–67, 131–139
See application file for complete search history.

(56) References Cited

U.S. PATENT DOCUMENTS

| 2,605,765 | A | 8/1952 | Kollsman |
| 3,886,938 | A | 6/1975 | Szabo et al. |
| 4,231,368 | A | 11/1980 | Becker |

(Continued)

FOREIGN PATENT DOCUMENTS

| CA | 2543545 | 5/2005 |
| DE | 196 27 619 A | 1/1998 |

(Continued)

OTHER PUBLICATIONS

Accu-Chek Spirit, "Pump Therapy Made for You," Roche, 2006, 6 pages.

(Continued)

*Primary Examiner* — Rebecca E Eisenberg
(74) *Attorney, Agent, or Firm* — Fish & Richardson P.C.

(57) ABSTRACT

A method and system for both autonomous and manual control of an infusion pump for delivering medication to a patient is provided.

16 Claims, 12 Drawing Sheets

(51) Int. Cl.
　　*A61M 5/142*　　(2006.01)
　　*A61M 5/315*　　(2006.01)

(56)　　　　References Cited

U.S. PATENT DOCUMENTS

| | | |
|---|---|---|
| 4,265,241 A | 5/1981 | Portner et al. |
| 4,300,554 A | 11/1981 | Hessberg et al. |
| 4,313,439 A | 2/1982 | Babb et al. |
| 4,493,704 A | 1/1985 | Beard et al. |
| 4,850,817 A | 7/1989 | Nason et al. |
| 5,045,064 A | 9/1991 | Idriss |
| 5,190,522 A | 3/1993 | Wojcicki et al. |
| 5,250,027 A | 10/1993 | Lewis et al. |
| 5,261,882 A | 11/1993 | Sealfon et al. |
| 5,314,412 A | 5/1994 | Rex |
| 5,335,994 A | 8/1994 | Weynant Nee Girones |
| 5,338,157 A | 8/1994 | Blomquist |
| 5,342,180 A | 8/1994 | Daoud |
| 5,395,340 A | 3/1995 | Lee |
| 5,411,487 A | 5/1995 | Castagna |
| 5,545,143 A | 8/1996 | Fischell et al. |
| 5,551,850 A | 9/1996 | Williamson et al. |
| 5,569,186 A | 10/1996 | Lord et al. |
| 5,626,566 A | 5/1997 | Petersen et al. |
| 5,637,095 A | 6/1997 | Nason et al. |
| 5,665,065 A | 9/1997 | Colman et al. |
| 5,669,877 A | 9/1997 | Blomquist |
| 5,719,761 A | 2/1998 | Gattie et al. |
| 5,741,216 A | 4/1998 | Hemmingsen et al. |
| 5,816,306 A | 10/1998 | Giacomel |
| 5,852,803 A | 12/1998 | Ashby, III et al. |
| 5,919,167 A | 7/1999 | Mulhauser et al. |
| 5,925,018 A | 7/1999 | Ungerstedt |
| 5,928,201 A | 7/1999 | Poulsen et al. |
| 5,947,934 A | 9/1999 | Hansen et al. |
| 5,951,530 A | 9/1999 | Steengaard et al. |
| 5,957,889 A | 9/1999 | Poulsen et al. |
| 5,984,894 A | 11/1999 | Poulsen et al. |
| 5,984,897 A | 11/1999 | Petersen et al. |
| 5,997,475 A | 12/1999 | Bortz |
| 6,003,736 A | 12/1999 | Ljunggren |
| 6,010,485 A | 1/2000 | Buch-Rasmussen et al. |
| 6,033,377 A | 3/2000 | Rasmussen et al. |
| 6,045,537 A | 4/2000 | Klitmose |
| 6,074,372 A | 6/2000 | Hansen |
| 6,110,149 A | 8/2000 | Klitgaard et al. |
| 6,156,014 A | 12/2000 | Petersen et al. |
| 6,171,276 B1 | 1/2001 | Lippe et al. |
| 6,231,540 B1 | 5/2001 | Smedegaard |
| 6,248,067 B1 | 6/2001 | Causey, III et al. |
| 6,248,090 B1 | 6/2001 | Jensen et al. |
| 6,248,093 B1 | 6/2001 | Moberg |
| 6,277,098 B1 | 8/2001 | Klitmose et al. |
| 6,302,855 B1 | 10/2001 | Lav et al. |
| 6,302,869 B1 | 10/2001 | Klitgaard |
| 6,375,638 B2 | 4/2002 | Nason et al. |
| 6,379,339 B1 | 4/2002 | Klitgaard et al. |
| 6,381,496 B1 | 4/2002 | Meadows et al. |
| 6,404,098 B1 | 6/2002 | Kayama et al. |
| 6,427,088 B1 | 7/2002 | Bowman, IV et al. |
| 6,461,331 B1 | 10/2002 | Van Antwerp |
| 6,474,219 B2 | 11/2002 | Klitmose et al. |
| 6,485,461 B1 | 11/2002 | Mason et al. |
| 6,508,788 B2 | 1/2003 | Preuthun |
| 6,524,280 B2 | 2/2003 | Hansen et al. |
| 6,533,183 B2 | 3/2003 | Aasmul et al. |
| 6,537,251 B2 | 3/2003 | Klitmose |
| 6,540,672 B1 | 4/2003 | Simonsen et al. |
| 6,544,212 B2 | 4/2003 | Galley et al. |
| 6,544,229 B1 | 4/2003 | Danby et al. |
| 6,547,764 B2 | 4/2003 | Larsen et al. |
| 6,551,276 B1 | 4/2003 | Mann et al. |
| 6,554,798 B1 | 4/2003 | Mann et al. |
| 6,554,800 B1 | 4/2003 | Nezhadian et al. |
| 6,558,320 B1 | 5/2003 | Causey, III et al. |
| 6,558,351 B1 | 5/2003 | Steil et al. |
| 6,562,001 B2 | 5/2003 | Lebel et al. |
| 6,562,011 B1 | 5/2003 | Buch-Rasmussen et al. |
| 6,564,105 B2 | 5/2003 | Starkweather et al. |
| 6,569,126 B1 | 5/2003 | Poulsen et al. |
| 6,571,128 B2 | 5/2003 | Lebel et al. |
| 6,577,899 B2 | 6/2003 | Lebel et al. |
| 6,582,404 B1 | 6/2003 | Klitgaard et al. |
| 6,585,644 B2 | 7/2003 | Lebel et al. |
| 6,585,699 B2 | 7/2003 | Ljunggreen et al. |
| 6,605,067 B1 | 8/2003 | Larsen |
| 6,613,019 B2 | 9/2003 | Munk |
| 6,641,533 B2 | 11/2003 | Causey, III et al. |
| 6,648,821 B2 | 11/2003 | Lebel et al. |
| 6,650,951 B1 | 11/2003 | Jones et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,659,978 B1 | 12/2003 | Kasuga et al. |
| 6,659,980 B2 | 12/2003 | Moberg et al. |
| 6,663,602 B2 | 12/2003 | Møller |
| 6,668,196 B1 | 12/2003 | Villegas et al. |
| 6,669,669 B2 | 12/2003 | Flaherty et al. |
| 6,687,546 B2 | 2/2004 | Lebel et al. |
| 6,690,192 B1 | 2/2004 | Wing |
| 6,691,043 B2 | 2/2004 | Ribeiro, Jr. |
| 6,692,457 B2 | 2/2004 | Flaherty |
| 6,692,472 B2 | 2/2004 | Hansen et al. |
| 6,694,191 B2 | 2/2004 | Starkweather et al. |
| 6,699,218 B2 | 3/2004 | Flaherty et al. |
| 6,702,779 B2 | 3/2004 | Connelly et al. |
| 6,715,516 B2 | 4/2004 | Ohms et al. |
| 6,716,198 B2 | 4/2004 | Larsen |
| 6,723,072 B2 | 4/2004 | Flaherty et al. |
| 6,733,446 B2 | 5/2004 | Lebel et al. |
| 6,736,796 B2 | 5/2004 | Shekalim |
| 6,740,059 B2 | 5/2004 | Flaherty |
| 6,740,072 B2 | 5/2004 | Starkweather et al. |
| 6,740,075 B2 | 5/2004 | Lebel et al. |
| 6,744,350 B2 | 6/2004 | Blomquist |
| 6,749,587 B2 | 6/2004 | Flaherty |
| 6,752,787 B1 | 6/2004 | Causey, III et al. |
| 6,758,810 B2 | 7/2004 | Lebel et al. |
| 6,768,425 B2 | 7/2004 | Flaherty et al. |
| 6,780,156 B2 | 8/2004 | Haueter et al. |
| 6,786,246 B2 | 9/2004 | Ohms et al. |
| 6,786,890 B2 | 9/2004 | Preuthun et al. |
| 6,796,970 B1 | 9/2004 | Klitmose et al. |
| 6,799,149 B2 | 9/2004 | Hartlaub |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,827,702 B2 | 12/2004 | Lebel et al. |
| 6,830,558 B2 | 12/2004 | Flaherty et al. |
| 6,852,104 B2 | 2/2005 | Blomquist |
| 6,854,620 B2 | 2/2005 | Ramey |
| 6,854,653 B2 | 2/2005 | Eilersen |
| 6,855,129 B2 | 2/2005 | Jensen et al. |
| 6,872,200 B2 | 3/2005 | Mann et al. |
| 6,873,268 B2 | 3/2005 | Lebel et al. |
| 6,878,132 B2 | 4/2005 | Kipfer |
| 6,893,415 B2 | 5/2005 | Madsen et al. |
| 6,899,695 B2 | 5/2005 | Herrera |
| 6,899,699 B2 | 5/2005 | Enggaard |
| 6,922,590 B1 | 7/2005 | Whitehurst |
| 6,936,006 B2 | 8/2005 | Sabra |
| 6,936,029 B2 | 8/2005 | Mann et al. |
| 6,945,961 B2 | 9/2005 | Miller et al. |
| 6,948,918 B2 | 9/2005 | Hansen |
| 6,950,708 B2 | 9/2005 | Bowman, IV et al. |
| 6,960,192 B1 | 11/2005 | Flaherty et al. |
| 6,979,326 B2 | 12/2005 | Mann et al. |
| 6,997,911 B2 | 2/2006 | Klitmose |
| 6,997,920 B2 | 2/2006 | Mann et al. |
| 7,005,078 B2 | 2/2006 | Van Lintel et al. |
| 7,008,399 B2 | 3/2006 | Larsen et al. |
| 7,014,625 B2 | 3/2006 | Bengtsson |

(56) References Cited

U.S. PATENT DOCUMENTS

| | | | |
|---|---|---|---|
| 7,018,360 B2 | 3/2006 | Flaherty et al. | |
| 7,018,361 B2 | 3/2006 | Gillespie et al. | |
| 7,025,425 B2 | 4/2006 | Kovatchev et al. | |
| 7,025,743 B2 | 4/2006 | Mann | |
| 7,029,455 B2 | 4/2006 | Flaherty | |
| 7,054,836 B2 | 5/2006 | Christensen et al. | |
| 7,104,972 B2 | 9/2006 | Møller et al. | |
| 7,128,727 B2 | 10/2006 | Flaherty et al. | |
| 7,133,329 B2 | 11/2006 | Skyggebjerg et al. | |
| 7,232,423 B2 | 6/2007 | Mernoe | |
| 7,295,889 B2 * | 11/2007 | Lahteenmaki | 700/233 |
| 7,617,132 B2 * | 11/2009 | Reade et al. | 705/26.61 |
| 2002/0027164 A1 * | 3/2002 | Mault et al. | 235/462.46 |
| 2002/0049482 A1 | 4/2002 | Fabian et al. | |
| 2002/0126036 A1 | 9/2002 | Flaherty et al. | |
| 2003/0032867 A1 * | 2/2003 | Crothall et al. | 600/300 |
| 2003/0050621 A1 | 3/2003 | Lebel et al. | |
| 2003/0065308 A1 | 4/2003 | Lebel et al. | |
| 2003/0088238 A1 | 5/2003 | Poulsen | |
| 2003/0163223 A1 | 8/2003 | Blomquist | |
| 2003/0163789 A1 | 8/2003 | Blomquist | |
| 2003/0208113 A1 | 11/2003 | Maulth et al. | |
| 2003/0212379 A1 * | 11/2003 | Bylund et al. | 604/504 |
| 2003/0233069 A1 | 12/2003 | Gillespie et al. | |
| 2004/0103043 A1 | 5/2004 | Reade et al. | |
| 2004/0128162 A1 | 7/2004 | Schlotterbeck et al. | |
| 2004/0171983 A1 | 9/2004 | Sparks et al. | |
| 2005/0038332 A1 | 2/2005 | Saidara et al. | |
| 2005/0095063 A1 | 5/2005 | Fathallah et al. | |
| 2005/0096637 A1 | 5/2005 | Heruth | |
| 2005/0160858 A1 | 7/2005 | Mernoe | |
| 2005/0171512 A1 | 8/2005 | Flaherty | |
| 2005/0192561 A1 | 9/2005 | Mernoe | |
| 2005/0222645 A1 | 10/2005 | Malave et al. | |
| 2005/0238507 A1 | 10/2005 | DiIanni et al. | |
| 2005/0245878 A1 | 11/2005 | Mernoe et al. | |
| 2005/0251097 A1 | 11/2005 | Mernoe | |
| 2005/0267402 A1 | 12/2005 | Stewart et al. | |
| 2005/0273059 A1 | 12/2005 | Mernoe et al. | |
| 2006/0036395 A1 | 2/2006 | Shaya et al. | |
| 2006/0041229 A1 | 2/2006 | Garibotto et al. | |
| 2006/0069382 A1 | 3/2006 | Pedersen | |
| 2006/0074381 A1 | 4/2006 | Malave et al. | |
| 2006/0095014 A1 | 5/2006 | Ethelfeld | |
| 2006/0135913 A1 | 6/2006 | Ethelfeld | |
| 2006/0142698 A1 | 6/2006 | Ethelfeld | |
| 2006/0178633 A1 | 8/2006 | Garibotto et al. | |
| 2006/0184119 A1 | 8/2006 | Remde et al. | |
| 2006/0200073 A1 | 9/2006 | Radmer et al. | |
| 2006/0206054 A1 | 9/2006 | Shekalim | |
| 2006/0247581 A1 | 11/2006 | Pedersen et al. | |
| 2007/0060869 A1 | 3/2007 | Tolle et al. | |
| 2007/0073228 A1 | 3/2007 | Mernoe et al. | |
| 2007/0073236 A1 | 3/2007 | Mernoe et al. | |
| 2007/0124002 A1 | 5/2007 | Estes et al. | |
| 2007/0156092 A1 | 7/2007 | Estes et al. | |
| 2007/0167905 A1 | 7/2007 | Estes et al. | |
| 2007/0167912 A1 | 7/2007 | Causey et al. | |
| 2008/0147050 A1 | 6/2008 | Mann et al. | |
| 2008/0198012 A1 | 8/2008 | Kamen | |
| 2008/0208627 A1 | 8/2008 | Skyggebjerg | |

FOREIGN PATENT DOCUMENTS

| | | |
|---|---|---|
| DE | 102 36 669 A | 2/2004 |
| EP | 0 496 141 | 7/1992 |
| EP | 0 612 004 | 8/1994 |
| EP | 0 580 723 | 10/1995 |
| EP | 1 045 146 | 10/2000 |
| EP | 1 136 698 | 9/2001 |
| EP | 1 177 802 | 2/2002 |
| EP | 0 721 358 | 5/2002 |
| EP | 1 495 775 | 1/2005 |
| EP | 1 527 792 | 5/2005 |
| EP | 1 754 498 | 2/2007 |
| FR | 2 585 252 | 1/1987 |
| GB | 747 701 | 4/1956 |
| GB | 2 218 831 | 11/1989 |
| WO | WO 90/15928 | 12/1990 |
| WO | WO 97/21457 | 6/1997 |
| WO | WO 98/11927 | 3/1998 |
| WO | WO 98/57683 | 12/1998 |
| WO | WO 99/21596 | 5/1999 |
| WO | WO 99/39118 | 8/1999 |
| WO | WO 99/48546 | 9/1999 |
| WO | WO 01/72360 | 10/2001 |
| WO | WO 01/91822 | 12/2001 |
| WO | WO 01/91833 | 12/2001 |
| WO | WO 02/40083 | 5/2002 |
| WO | WO 02/057627 | 7/2002 |
| WO | WO 02/100469 | 12/2002 |
| WO | WO 03/103763 | 12/2003 |
| WO | WO 2004/056412 | 7/2004 |
| WO | WO 2004/110526 | 12/2004 |
| WO | WO 2005/002652 | 1/2005 |
| WO | WO 2005/039673 | 5/2005 |
| WO | WO 2005/072794 | 8/2005 |
| WO | WO 2005/072795 | 8/2005 |
| WO | WO 2006/105792 | 10/2006 |
| WO | WO 2006/105793 | 10/2006 |
| WO | WO 2006/105794 | 10/2006 |

OTHER PUBLICATIONS

Debiotech News Release, "Debiotech reveals its new miniaturized Disposable Insulin Nanopump™ for Diabetes therapy," available at http://www.debiotech.com/news/nw_159.html Apr. 24, 2006, 3 pages.

Medtronic News Release, "Medtronic Receives FDA Approval for World's First Insulin Pump with Real-time Continuous Glucose Monitoring," Apr. 13, 2006, 3 pages.

OmniPod Insulin Management System-Investor Relations- Press Release, Feb. 1, 2005, http://investors.insulet.com/phoneix. zhtml?c=209336&p=irol-newsArticle&ID=988708&highlight=1 page.

OmniPod Quick Start Guide, 2007, 2 pages.

Patent Abstracts of Japan, vol. 1999, No. 04, and JP 11 010036 , Apr. 30, 1999 and Jan. 19, 1999, Toray Ind. Inc.

The Medtronic Diabetes Connection, 2006, 6 pages.

Xilas Temp Touch, "The latest in high-tech and convenient devices," DOCNews, vol. 2, No. 7, Jul. 1, 2005, http://docnews.docnews. diabetesjournals.ord/cgi/content/full/2/7/13, 3 pages.

International Search Report and Written Opinion in International Application No. PCT/US2006/043845, mailed Aug. 22, 2007, 16 pages.

International Preliminary Report on Patentability in International Application No. PCT/US2006/043845, mailed May 22, 2008, 10 pages.

Walsh et al., "Guidelines for Optimal Bolus Calculator Settings in Adults", J. Diabetes Science and Technology; vol. 5 Issue 1; Jan. 2011, pp. 129-134.

Walsh et al., "Guidelines for Insulin Dosing in Continuous Subcutaneous Insulin Infusion Using New Formulas from a Retrospective Study of Individuals with Optimal Glucose Levels", J. Diabetes Science and Technology, vol. 4 Issue 5, Sep. 2010, pp. 1174-1181.

* cited by examiner

METHOD AND SYSTEM FOR MANUAL AND AUTONOMOUS CONTROL OF AN INFUSION PUMP

CROSS-REFERENCE TO RELATED APPLICATIONS

This application is a division of U.S. application Ser. No. 13/468,669 filed on May 10, 2012, which is a division of U.S. application Ser. No. 11/557,926 filed on Nov. 8, 2006, which claims the benefit of U.S. provisional application 60/734,398, filed Nov. 8, 2005. The disclosures of these prior applications are considered part of and are hereby incorporated in its entirety by reference in the disclosure of this application.

TECHNICAL FIELD

The present invention relates to autonomous and manual control of an infusion pump.

BACKGROUND

An infusion pump is used to infuse fluids, medication or nutrients into a patient's circulatory system. It is generally used intravenously, although subcutaneous, arterial and epidural infusions are occasionally used.

Infusion pumps can administer fluids in ways that would be impractically expensive or unreliable if performed manually. For example, infusion pumps can administer 1 mL per hour injections (too small for a drip), injections every minute, injections with repeated boluses requested by the patient, up to the maximum number per hour allowed (e.g. in patient-controlled analgesia), or fluids whose volumes vary by the time of day.

As infusion pumps can also produce quite high but controlled pressures, the pumps can inject controlled amounts of fluids subcutaneously (beneath the skin), or epidurally (just within the surface of the central nervous system—a very popular local spinal anesthesia for childbirth).

SUMMARY

A method and system is provided for both autonomous and manual control of an infusion pump for delivering medication to a patient. The manual control may provided by an onboard assistance device allowing the user to make entries and corrections.

A method for directly transferring operating parameters from one infusion pump device to a second infusion pump device is described that includes providing a first infusion pump device including parameters to be transferred, establishing a communications link from the first infusion pump device to a second infusion pump device, and transferring the parameters from the first infusion pump device to the second infusion pump device.

Variously, the communication link may be established using wired means, by contact between the first infusion pump device and the second infusion pump device, or by using wireless means. Variously, the parameters may include historical treatment information, may include user information, or may include operating parameters.

A method of entering food information into an infusion pump system is described that includes providing a foodstuff identification, and using device assisted data entry to enter the foodstuff identification into an infusion pump system. The method may also include using the entered foodstuff identification to retrieve foodstuff composition information.

Variously, the foodstuff identification may include a barcode, or may include an RFID tag. Variously, the foodstuff identification may be entered using a scanner in an infusion pump system, or may be entered using an RFID reader in an infusion pump system.

An infusion pump system is described that includes an infusion pump body, a control system, and an RFID reader, wherein the RFID reader is in communication with the control system. The RFID reader may be contained within the infusion pump body, or form part of the infusion pump body.

A method for temporarily disabling a disruptive alert of an infusion pump system is described that includes receiving a request to disable disruptive alerts from an infusion pump system for a specified period of time, disabling disruptive alerts from the infusion pump system for the specified period of time, and re-enabling disruptive alerts after the specified period of time has passed. Health alerts may remain active during the specified period of time.

Variously, the specified period of time may be determined by the difference between the current time and a requested time, or the specified time may be determined by a request for a specified time period.

A method of determining a treatment amount for an infusion pump system is described that includes obtaining treatment information including foodstuff composition information, food on board information, and insulin on board information, and determining a recommended bolus amount based on the treatment information.

Variously, the foodstuff composition information may include a carbohydrate ratio, may include quantity information, or may include carbohydrate, fat, and protein information.

The method may also include using user metabolism information in calculating a bolus amount. Variously, user metabolism information may include insulin sensitivity information, or glucose sensitivity information.

A method of determining a treatment amount for an infusion pump system is described that includes obtaining foodstuff composition information including carbohydrate, fat, and protein composition information of a foodstuff; and determining a recommended bolus amount based on the foodstuff composition information.

Determining a recommended bolus amount may also be based on user metabolism information, or may also be based on a user's food on board and insulin on board information. The foodstuff composition information may be entered into the infusion pump system using device assisted data entry.

A method of determining a recommended bolus amount is described that includes obtaining user metabolism information, obtaining foodstuff composition information including carbohydrate, fat, and protein composition information using device assisted data entry, and determining a recommended bolus amount using the following equation:

$$\text{Recommended bolus amount} = \text{Food Now} \ast \text{Carb Ratio} + (BG - BG\text{target}) \ast \text{insulin sensitivity} - IOB + FOB,$$

where:
IOB=f(t)*bolus;
FOB=f(t)*grams Carb Ratio+f(t)*grams Protein Ratio+f(t)*grams Fat ratio; and
Food Now=the amount and type of foodstuffs ingested expressed in terms of grams, carbohydrates, proteins or fat.

The details of one or more embodiments of the invention are set forth in the accompanying drawings and the descrip-

DETAILED DESCRIPTION

A method and system for autonomous and manual control of an infusion pump system is described. The system may receive input, analyze input, display some or all analysis data to an infusion pump user, and may perform modifications to one or more infusion pump parameters. The infusion pump system may automatically prompt the user to perform a system task or modification. For example, when a blood glucose ("BG") reading is dangerously high in the pump user, the system may prompt the user with information regarding decisions on dispensing medication or nutrients into the pump user's circulatory system, such as insulin medication to lower the BG level in the user. The user can then perform various tasks, including, but not limited to, ignoring the prompt, implementing the suggested protocol, or modifying the suggested protocol before implementing the modified protocol. In one embodiment, upon receiving a user requested modification, the system may present and display information to the user indicating that the infusion pump parameters should remain unchanged.

The methods described in this application can be performed manually based on a request from a pump user, automatically based on previously entered user data (e.g., an alarm or criteria set by the user), or a combination of both. The manual control may be provided by an onboard assistance system to allow the pump user to make entries and corrections in the system.

Figure 1:
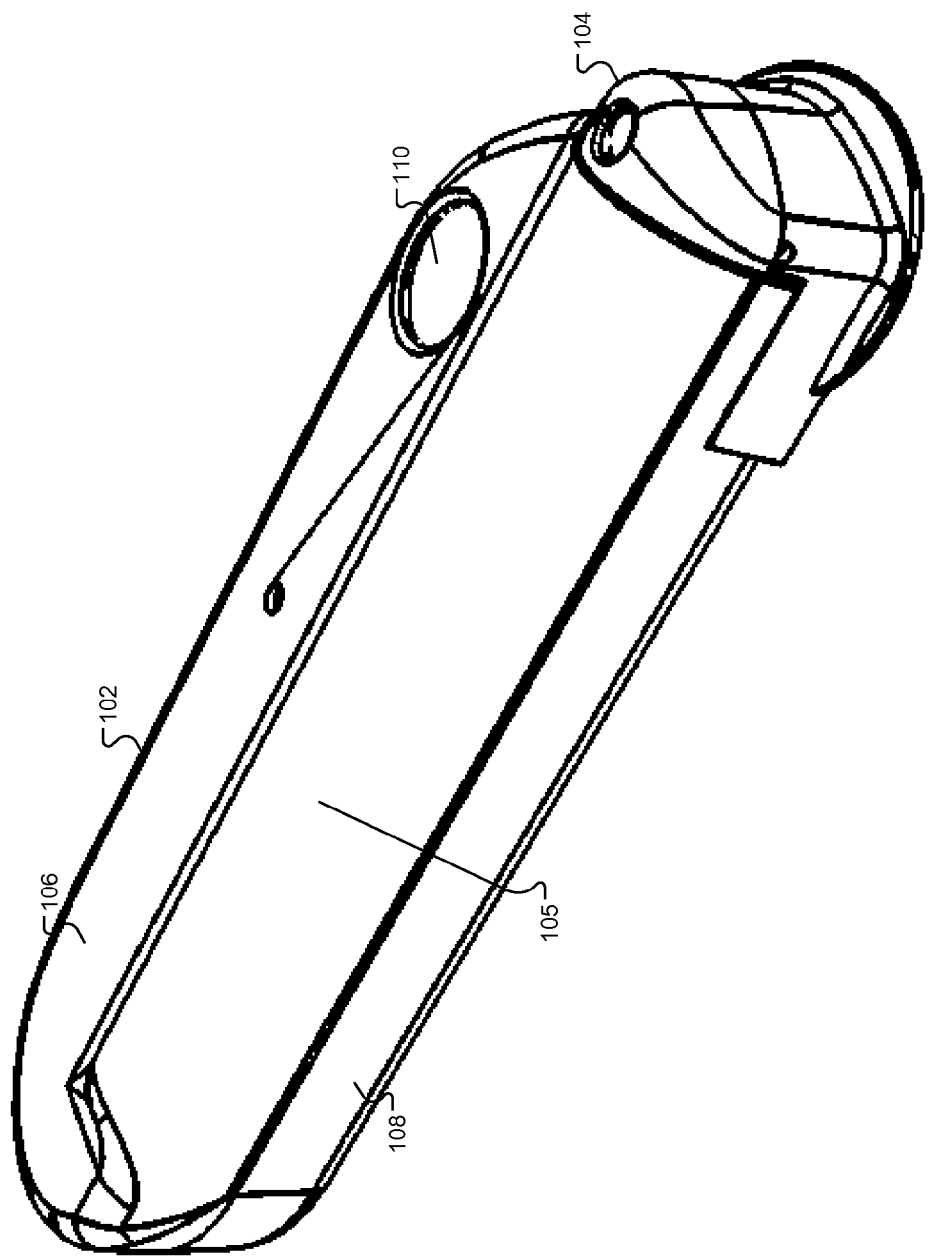
FIG. 1 is an illustration of an exemplary infusion pump system.

FIG. 1 is an illustration of an exemplary infusion pump system 100 that may be used to perform the methods described in this disclosure.

The infusion pump system 100 includes a pump body 102, an infusion site interface 104, and a reservoir 105. The pump body 102 includes an upper housing 106 and a lower housing 108 which define a periphery in which the mechanisms of a pump unit reside. The upper and lower housings 106, 108 may include openings or penetrations for attachment and guidance of the infusion site interface 104 to the pump body 102. Additionally, openings in the pump body may allow for the installation of the reservoir 105 contained within the pump body 102, and maintenance of the reservoir 105 that may be in communication with the infusion site interface 104 for dispensing medication. In general, the infusion site interface 104 may provide for continuous or intermittent subcutaneous fluid infusion. One or more buttons 110 may be used to enter user requests into the pump system.

Figure 2:
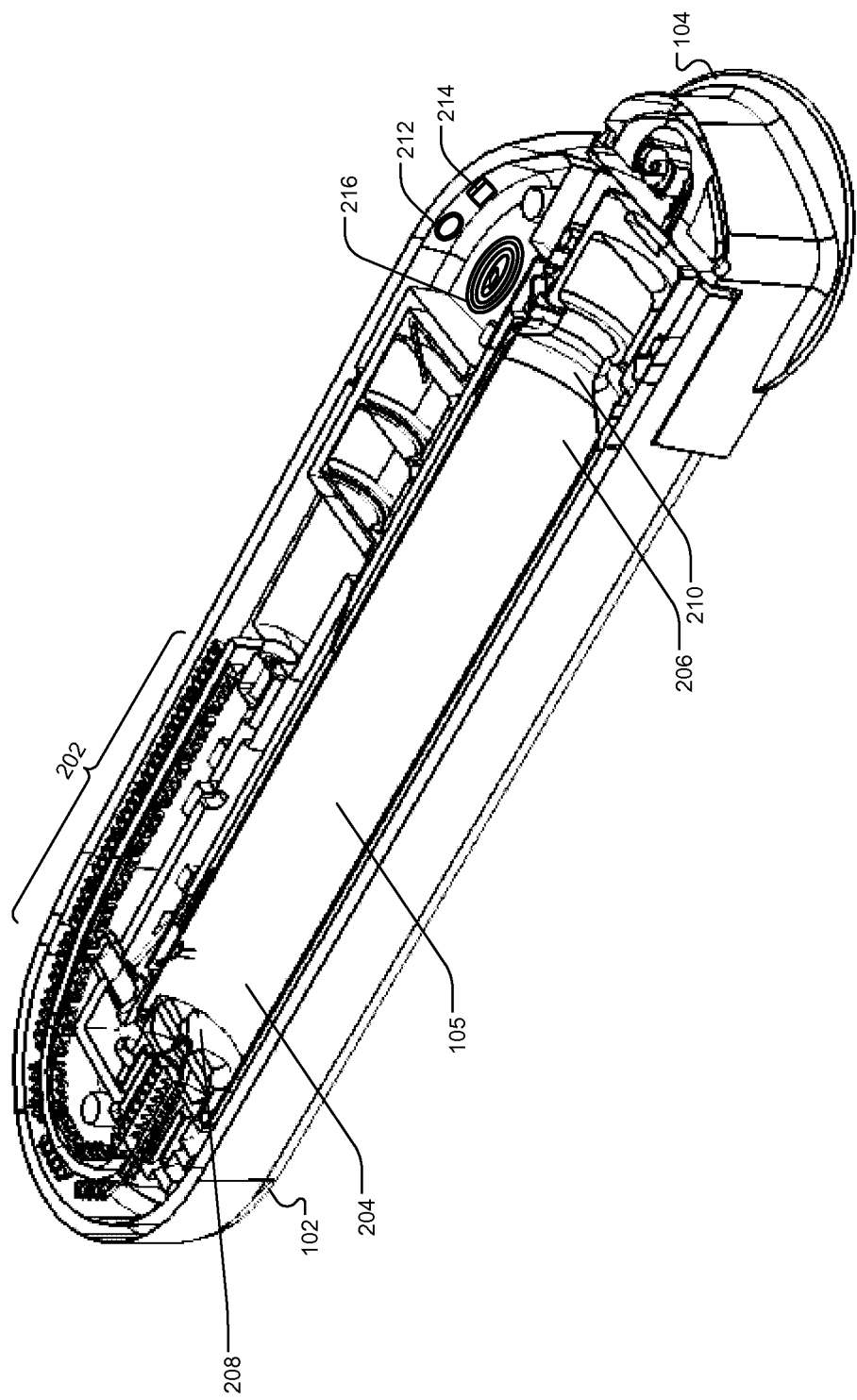
FIG. 2 is an illustration of a cross sectional view of the exemplary infusion pump system of FIG. 1.

FIG. 2 is an illustration of a cross sectional view of the exemplary infusion pump system of FIG. 1.

As shown, a mechanism is contained in the pump body 102 that comprises the reservoir 105, a drive mechanism 202 and a control system (not shown). The reservoir 105 is comprised of a distal end 204 and a proximal end 206, and is cylindrical in geometry with the distal end 204 sealed by a moveable plunger 208 of matching geometry as the reservoir 105 and the proximal end 206 are contained by a pump body septum 210. The infusion pump system 100 generally dispenses fluid when the drive mechanism 202 is actuated, thereby applying pressure internal to the reservoir, such that a substance contained within the reservoir may be driven through a device (not shown) that may pierce the pump body septum 210. The actuation of the drive mechanism 202 may be governed by the control mechanism. The geometry of the reservoir 105 has been shown as cylindrical for illustrative purposes only and as such, the reservoir 105 is geometry independent.

In addition to the functionality of the pump system, the system may also include communication circuitry and functionality to upload, download or otherwise transfer data to and from the pump system. For example, the infusion pump system 100 may transfer, upload, or download data to a computer, a data repository, to itself, or to another infusion pump, to name a few examples. In particular, the infusion pump system 100 may include circuitry designed for sending and receiving data, such as communication chipsets including, but not limited to, universal serial bus (USB), RS-232, Ethernet, Bluetooth, radio frequency, infrared, wireless Ethernet, or other such technologies. As shown in FIG. 2, the system 100 may include an infrared port 212, a USB port 214, and a radio frequency identification (RFID) reader 216. In some implementations, rather than having an internal RFID reader, the infusion pump system may include circuitry for connecting an external RFID reader. In some implementations, some, all, or none of the above communication chipsets, connectors, or technologies may be included in the system, and as such, other ports and connector technologies are possible.

In some implementations, additional communication ports (not shown) may be available for connecting peripheral data collection devices. The data collection devices may be used to enter input into the infusion pump system. The data collection devices may include, but are not limited to, a bar code scanner, a radio frequency (RF) reader, an optical scanner, an infrared scanner, or other wired or wireless data collection device. The data collection device may allow data to be uploaded or entered into the pump system by selecting or scanning food and medication information, for example. In some implementations, the pump user may download data from a website, or other means where wired or wireless communication is available (e.g., a mobile telephone, or a personal digital assistant (PDA)).

The pump user may collect data for the infusion pump system in various ways. Device assisted data entry may be utilized to obtain additional information beyond that which may be easily entered using a manual approach. For example, a pump user may user the USB port 214 to plug in a barcode scanner, and can scan foodstuffs to obtain additional information, such as carbohydrate, fat, and protein amounts, mass, brand, food group, or other foodstuff identifying features. In other implementation, the infusion pump system may include an on-board barcode scanner. Using a barcode scanner, the user may scan the foodstuff item and enter one or more identifying features in the user interface. In some implementations, the pump user may use an onboard RFID reader 216 to scan RFID tags located on foodstuffs, rather than a barcode reader. In other implementations, a RFID reader may be plugged in a USB port or other input/output port. In other implementation, other device assisted data-entry approaches may be used. Furthermore, in other embodiments, wireless device assisted data entry implementations may be used (e.g., a wireless RFID reader or wireless barcode scanner may be used to communicate foodstuff information to the infusion pump system).

In some implementation, the foodstuff information may include a product identifier or code. The product identifier or code may be used to obtain additional product information from an onboard data repository. Thus, a UPC code may be used to identify a foodstuff, which is then looked up in a data repository to obtain nutrition and other information regarding the foodstuff.

Collecting data in the infusion pump system may be advantageous when calculating treatment methods for pump users. For example, data collection devices may also provide a method for entering food identification and composition information. The composition information may comprise a carbohydrate ratio, quantity information, carbohydrate content, fat content, or protein content. In some implementations, the collected data may be used to determine and recommend a particular bolus amount.

Figure 3:
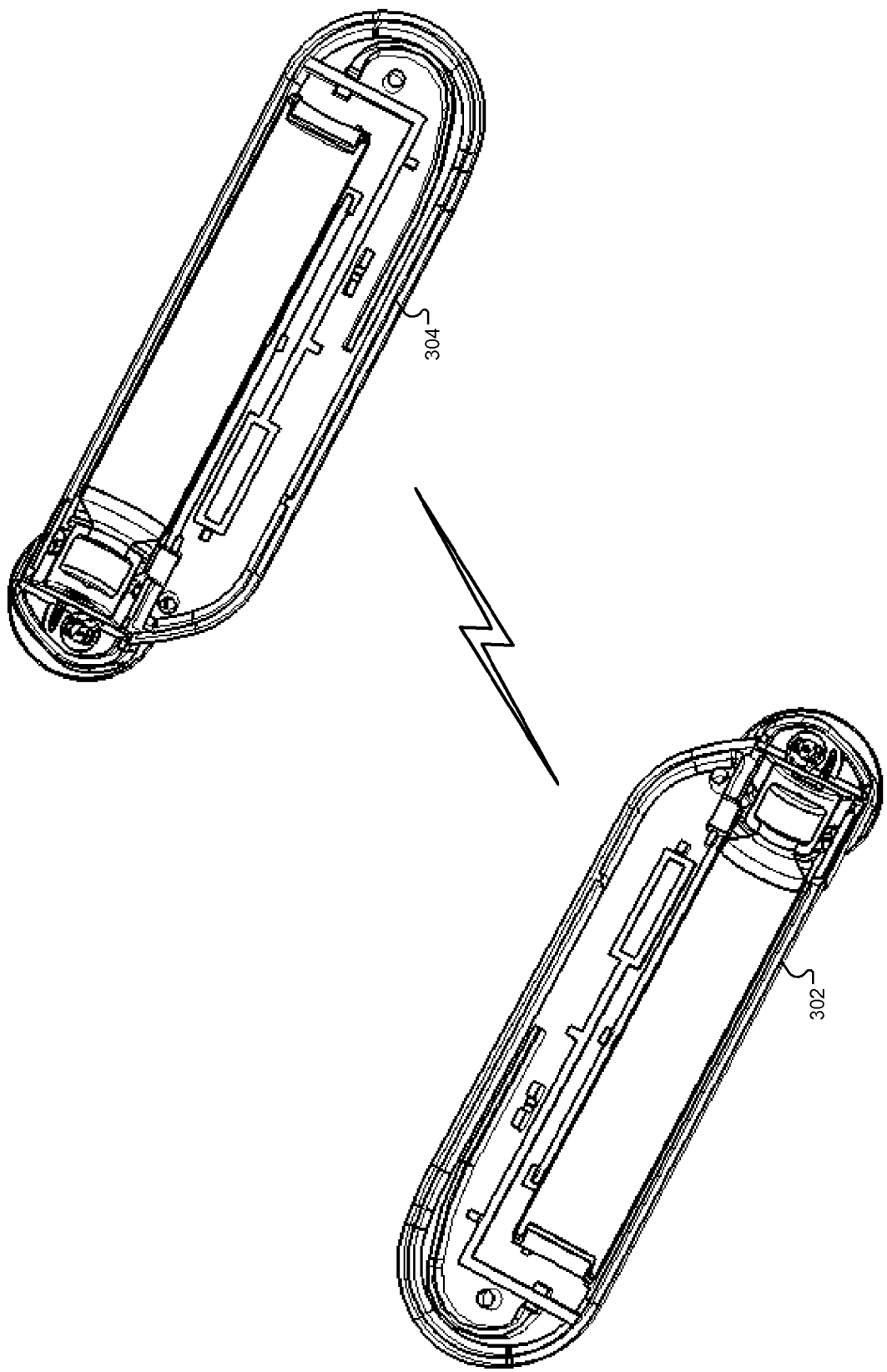
FIG. 3 is an illustration of transferring data between two infusion pump systems.

FIG. 3 is an exemplary illustration of transferring data between two infusion pump systems.

In general, a first pump 302 and a second pump 304 may establish pump-to-pump communications to transfer data between the pumps. Specifically, one or more communication ports on the pumps may initiate the communication. For example, an infrared port on the first pump 302 may initiate communication with an infrared port on the second pump 304 upon coming into close proximity. In some implementations, the communication may be a wired communication where a pump user has "connected" the pumps together (e.g., as in a USB to USB cable connection). Regardless of which pump initiated the connection, a portion of data may be bi-directionally transferred between both pumps, as facilitated by a pump user. In some implementations, no data may be transferred (e.g., when a pump user has not requested a transfer).

After the communication protocol is established, the transferring of data may commence. In particular, the processing devices on each pump may invoke their respective data repositories to begin transferring data between the pumps. In general, operating parameters, historical treatment data, user information, configuration data, pump user data, pump manufacturer data, medication on board, and other system information may be transferred from one pump to another pump.

Figure 4:
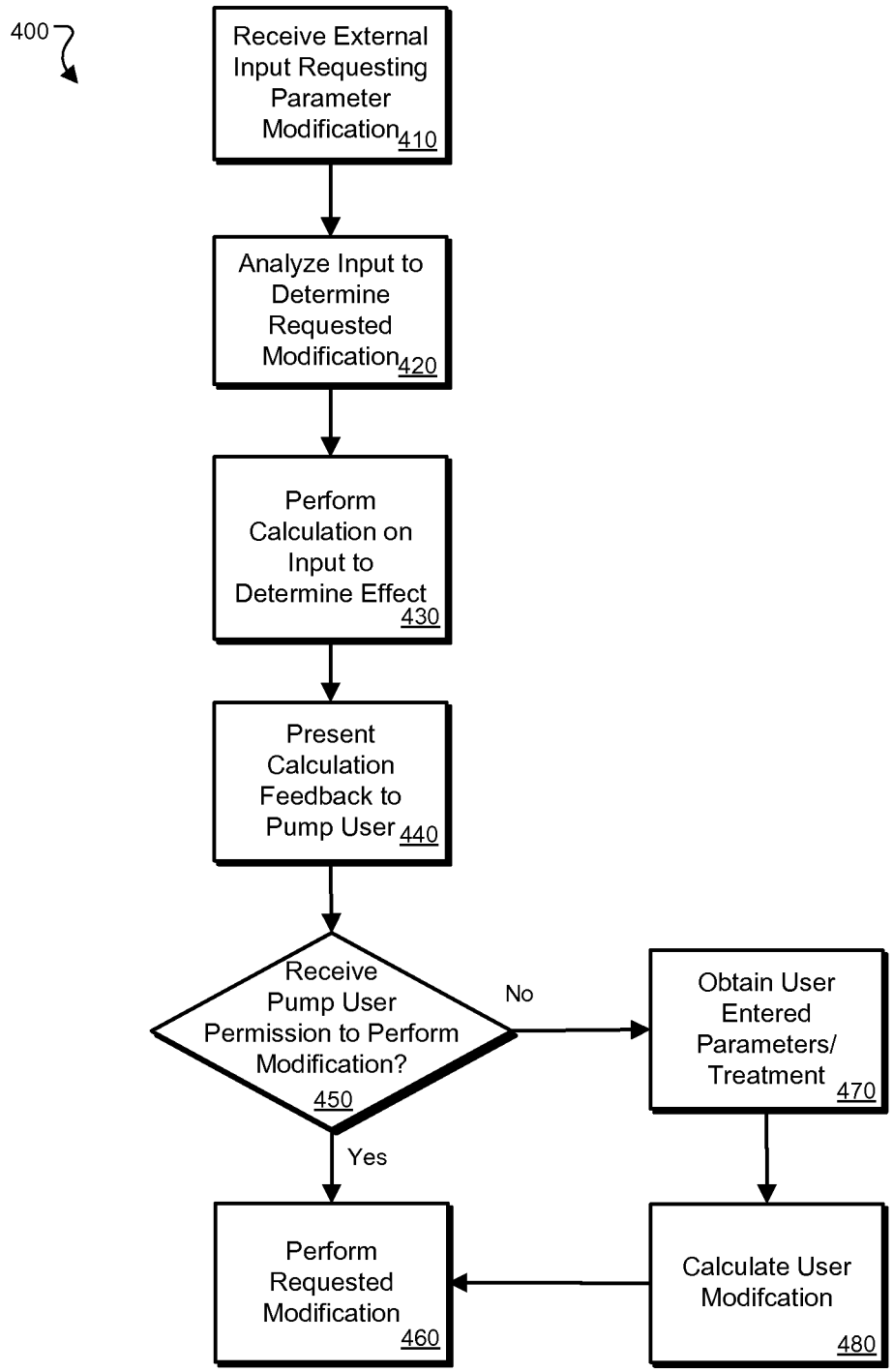
FIG. 4 is a flow chart illustrating a method of assisted modification of infusion pump parameters.

FIG. 4 is a flow chart illustrating a method 400 of assisted modification of infusion pump parameters.

The method 400 will be described in reference to an infusion pump system that processes user requests and infuses fluids, medication, nutrients or other materials into the body of the pump user. The user requests may include various modifications to system operating parameters, such as modifications to bolus profile, basal rate, RTC, BG history, delivery history, bolus history, and others. The list of operating parameters described above is not an exhaustive list and as such, other parameters may be modified manually or autonomously in the system.

The method 400 begins with the receipt 410 of an external input. The input may include updates for FOB information, IOB information, medication details, or simply include a request for modification of one or more system parameters. The input can be manually entered into the infusion pump via a control center, graphical user interface, bar code reader, radio frequency (RF) reader, optical reader, infrared reader, wireless transmission, email, text message, Internet, or other means.

After the input is received, and after any optional pre-processing, the infusion pump may analyze 420 the received data to determine whether the input is a request to modify, or other system task. For example, a request for performing a calculation in the system may be carried out immediately, since the effect of performing the calculation is informational to the user (e.g., the calculation does not change a treatment parameter and may therefore be completed upon request). However, some requests include modifying medication levels or rates may require further analysis to determine whether or not to carry the request out, as received. When modifications are requested or proposed, further processing may be carried out using system data, input data, or stored data, and the user may be prompted to approve such modifications.

Upon completion of the analysis, further calculations may be performed 430 to determine what effect, if any, the modification may have on the pump user. For example, a diabetic pump user may manually enter a food item that is about to be consumed. The pump user may wish to preemptively view FOB values and the corresponding bolus amount of insulin that will be infused if the user consumes the entered food. Here, the calculation can be performed and a suggested bolus amount can be presented to the pump user.

Calculation feedback, instructions, or other information may be presented 440 to the user audibly, visually, or via another sense, such as a vibration (e.g., such that the user can feel an alarm is being generated). Typically, the information is displayed to the user in a user interface, but multiple modes of presentation may be possible. Upon presentation of the information, the user may input further information, make selections, or ignore the display.

In some implementations, the system may inquire about performing processes in the infusion pump. For example, the infusion pump may query the pump user to impart permission to perform 450 a modification in the system. In this example, a request may have generated the query, or alternatively, the system may automatically generate the query to request permission for performing a system function. In some implementations, a query may display to inquire about a preprogrammed event, such as a treatment change.

The pump user may receive queries in the graphical user interface that pertain to system processes, parameters, events, or other items. The user may choose to respond to a query or request from the pump system. In the event that a query is generated requesting permission to perform a system parameter modification, the user may choose to accept the modification. Upon receiving permission to perform the intended modification, the infusion pump system can perform 460 the requested modification.

Alternately, the pump user may disapprove of a particular modification and thus may refuse permission to perform the modification. Additionally, the user may refuse permission and may enter modified information. The modified information can be applied and the query may be regenerated such that the user can be presented the same query with the updated information. In some embodiments, input from the user may be accepted and implemented immediately and the system may not present another query to the user. The infusion pump system can obtain 470 the user entered parameters or treatment correction and calculate 480 an appropriate modification. Upon determining the modification requested, the pump system may carry out 460 the requested modification(s). In some implementations, the received input may not be a correction or modification, but instead may be additional information for the system to further process.

In some implementations, a user may input a request to modify a system parameter, but inadvertently leave out a digit or instruction regarding the parameter. In the event that data is missing or entered incorrectly, the system may not make the requested modification. In some implementations, an indication of missing data may trigger an indicator, such as a display to the user, enabling the user to notice and correct the error.

Figure 5:
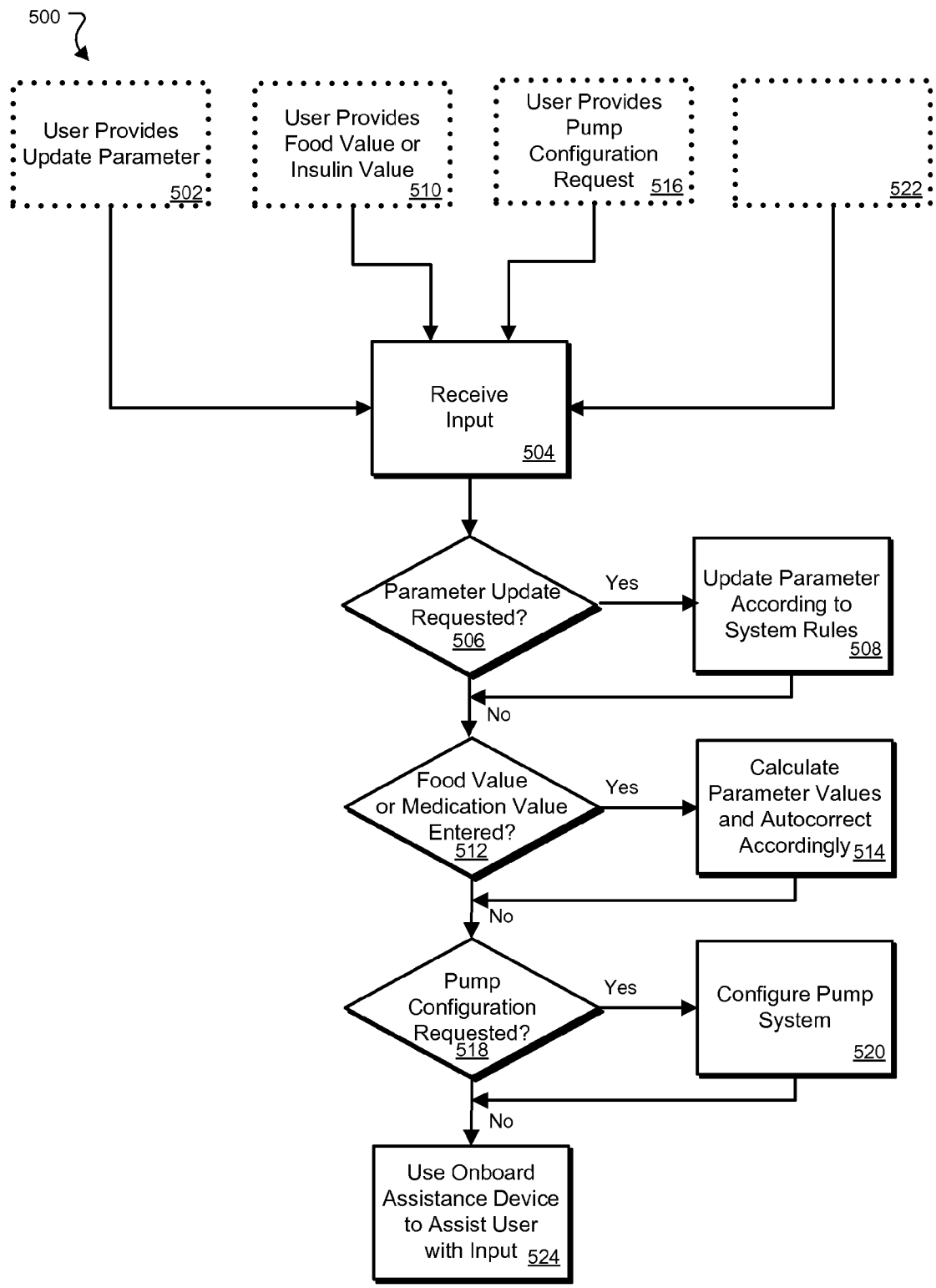
FIG. 5 is a flow chart illustrating a method of providing external input to modify infusion pump parameters.

FIG. 5 is a flow chart illustrating a method 500 of providing external input to modify infusion pump parameters.

The method 500 will be described in reference to an infusion pump system that can receive input. Variously, pump users or medical staff can provide information to the pump system in various ways, including manual entry, or data entry by other methods, such as a transmission, automated data entry, or other method. In one embodiment, the user may provide updates for one or more system operating parameters, such as a bolus profile, basal rate, RTC, or BG history to name a few examples. In another embodiment, the user may provide food values or medication values to assist the pump system with future processing of calculations. In yet another embodiment, the user may provide a pump configuration request, whereby the pump system can reconfigure itself according to the input, or alternatively, the pump system can download or upload pump contents in preparation for a pump replacement. Other manually entered input may be possible.

The method 500 begins by receiving one or more inputs from the user. If the user inputs 502 update parameters, the system may receive 504 the input in a control module, for example. The control module may determine the type of information entered. Accordingly, this may involve one or more queries to determine the purpose of the entry. Thus, the system may assess 506 whether or not a parameter update is being requested by the user. If the entered input is indeed a parameter update, the system may update 508 the parameter according to system rules. System rules may include various error checking mechanisms to ensure a particular parameter update does not endanger the health of the pump user. Upon completing the parameter update, the system may await another input from the user. The pump system may receive several entries and may have to distinguish between several types of input.

In some implementations, the user may enter 510 a food or medication value into the system, instead of a parameter update as described above. The control module may determine 512 the type of information entered by the user. If the input is a food value or medication value, the system may perform processing steps to recalibrate parameter values such that the pump system functions to the user's advantage. For example, the user may enter food values for food about to be consumed. Accordingly, the pump system can perform calculations 514 to determine accurate treatment values for the user in the next several hours, for example.

In some implementations, the user may enter 516 pump configuration requests, such that a pump can be reconfigured or configured upon replacement. Here, the system may again use the control module to determine 518 the type of information entered by the user. The configuration request may simply include resetting certain system parameters, while leaving others intact. In another example, the user may request configuration of a newly installed pump system (e.g., upon replacement of an old pump system). Upon determining that the user has requested a pump configuration, the system may perform 520 the configuration of the pump system.

The user may also enter 522 other types of input that the system may or may not recognize upon entry. For example, a database having various food values and their typical masses may be downloaded to the pump system. Here, the database can be used to compare typical "servings" of food items against what a user may consume. In this example, the database may be uploaded wirelessly from the Internet and may require further user interaction to appropriately store and use the database in the pump system. As such, an onboard assistance device may assist 524 the user in walking through configuration steps to ensure the database operates properly. The onboard assistance device may also intervene to assist the user for other unknown data entries.

Figure 6:
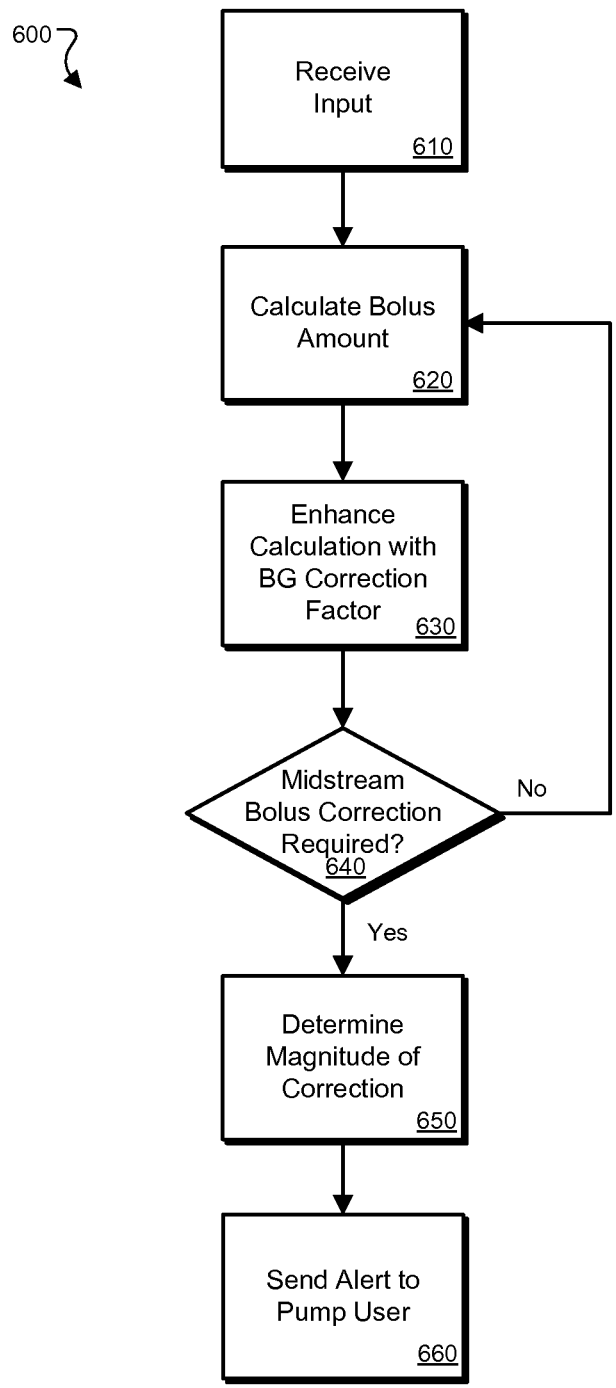
FIG. 6 is a flow chart illustrating a method of analyzing received criteria to determine or enhance a bolus amount in an infusion pump system.

FIG. 6 is a flow chart illustrating a method 600 of analyzing received criteria to determine or enhance a bolus amount in an infusion pump system.

The method 600 will be described in reference to an infusion pump system that analyzes user input to determine system parameter values, such as bolus amounts and rates. The method 600 may provide manual control of the infusion pump system by means of a device or program which assists the pump user with determining proper bolus amounts.

A healthy human body regulates insulin levels in the bloodstream using the pancreas organ. Insulin production relates closely to the rise of BG levels in the body (e.g., when glucose levels rise, insulin levels rise). A diabetic patient is unable to maintain consistent insulin levels and proper insulin response, and may require external means to assist in regulating their insulin levels. Insulin pump therapy may infuse insulin into fatty tissues just beneath the surface of the skin in a diabetic patient. This may create a delay in the absorption of insulin into the bloodstream.

Typically, insulin levels rise well after a rise in glucose level, thus, timing is a key issue in the delivery of insulin. This can make it difficult to adjust insulin levels in the body to an appropriate level. This may be compounded by the fact that most diabetics test their BG levels after they finish eating, sometimes significantly later than the start of the meal. Accordingly, external systems such as infusion pumps may be designed to account for time anomalies and the like when delivering medication to a pump user.

In addition, users may have different profiles as relate to digestion and metabolism. For example, a user may have different glucose sensitivity than other users, and be able to tolerate a higher or lower level of glucose. These particular individuals' metabolism may correlate to different glucose levels in the blood as a result of the same specific food intake. As another example, a user may have different insulin sensitivity in which the same amount of insulin will have a different effect on the Blood glucose level in the bloodstream. In addition, the metabolism time of glucose and insulin for one user may be faster or slower than for other users.

The method 600 begins when the infusion pump system receives 610 input from a pump user. For example, food on board (FOB) and insulin on board (JOB) values can be received in the pump system. FOB is a measurement of food previously consumed by a user. In one embodiment, FOB is a measurement of food that has been consumed by a user, but not yet converted into glucose usable by the body for metabolism. IOB is a measurement of the insulin previously dosed to a user. In one embodiment, IOB is a measure of the insulin that has been dosed to a user but not yet available for the metabolic process (i.e., insulin that has not yet been absorbed into the bloodstream). In another embodiment, IOB is a measure of the total insulin in a user's system, including insulin in the bloodstream or in the tissues. Thus, it may be a measure of all insulin that has not yet been metabolized.

In various embodiments, the system may use the FOB and IOB to calculate bolus amounts. Using more powerful microprocessors, pumps may be designed to determine and utilize information concerning the individual user. In various embodiments, individual parameters such as sensitivity to insulin, carbohydrates or other endocrine information may allow the pump to improve recommended treatments. In some implementations, the pump system may utilize food input and BG level input to accurately determine when a particular meal was started, when a peak glucose level will occur, and/or what an uncorrected BG level should be.

An onboard assistance system may include a processing method, for example, which incorporates carbohydrate, protein, and fat values to determine a value for food on board ("FOB") for the user. The FOB calculation might correspond to the equivalent amount of carbohydrate for each of the protein and fat intakes. As such, the pump user may request a task, and be given further assistance by the onboard assistance system to carry out the task with accuracy.

The onboard assistance program may include a monitoring method that incorporates previously entered data and treatment information to determine a value for insulin on board ("IOB") for the user. In general, an IOB feature in a pump calculates the decay of insulin in the body after a bolus of insulin is given to a pump user. The infusion pump system may recognize current dosage levels that a user is receiving and further, can measure the dosage to determine future infusion dosages or rates. The pump user can input several variables that the pump system can utilize to recommend one or more treatments. Advantageously, using an infusion pump having manual and autonomous control properties may allow an accurate estimate of a particular bolus rate or amount. In addition, the pump user may have flexibility in entering and modifying the bolus rate or amount at any time.

In one embodiment, a recommended bolus amount may be determined 620 using the following equation:

Recommended bolus amount=Food Now*Carb Ratio+
(BG−BGtarget)*insulin sensitivity IOB+FOB where:
IOB=f(t)*bolus
FOB=f(t)*grams Carb Ratio+f(t)*grams Protein Ratio+f(t)*grams Fat ratio
Food Now=the amount and type of foodstuffs ingested expressed in terms of grams, carbohydrates, proteins or fat.

The bolus amount determined by the above equation may be modified or enhanced 630 based on a BG correction factor. The BG correction factor may be calculated as the difference between the measured BG level and the target BG level. This difference, if any, may assist the pump user in determining if a midstream bolus correction factor is required or desired, as well as determine the potential magnitude of correction. In general, the measured BG level is a function of time against foodstuffs intake and calculated by the formula described above.

In some implementations, the BG correction factor may be determined by the maximum BG level whereby the maximum BG level is an individually determined number. The maximum BG level may be based on factors including prior history, experience, and desired treatment levels, and may be set by the user or a health care provider. The maximum BG level may be input and the bolus correction factor may then be calculated based on the maximum BG level. This may assist the pump user in determining if a midstream bolus correction factor may be required or desired, as well as determining the potential magnitude of correction.

In some implementations, the maximum allowable BG may be provided as input to the pump. In this example, the pump may analyze the input and suggest an appropriate bolus amount and corresponding timing. This information may also allow the pump to suggest 640 midstream corrective actions, such as a modification to an immediate or delayed bolus, additional BG checks or other recommended changes such as temporary suspension of therapy. If the infusion pump suggests a midstream bolus correction, a magnitude of correction can be determined 650 in the pump system. In one embodiment, the infusion pump may calculate a bolus amount based on information including the total intake of grams of carbohydrates, fat and protein, as well as the timing of the intake. A bolus amount may be recommended by calculating 620 system parameters. The outcome of the calculations may be made available 660 to the pump user in the user interface, for example.

In some implementations, a delayed bolus feature may be implemented to provide further precision in controlling a pump user's BG levels. For example, anticipating what a BG level may be after consumption of an entered foodstuff may allow the pump system to properly dose the pump user at an opportune time. In some implementations, the delayed bolus may be user selectable. For example, pump users may enter the time at which a particular foodstuff was consumed and set a time to receive a dose of insulin.

The modified treatment amount determined by the pump system may include the use of additional factors not normally used in infusion pump systems such as insulin pumps. The advantages of using additional information may include obtaining a treatment that is individually suited to the user, obtaining a treatment that has a better time profile to better match actual food consumption and medicament infusion, obtaining a treatment based on additional foodstuff information, or obtaining a treatment that is based in part on user metabolism. The additional information may be available due to increased processing and memory abilities, new ways of looking at ways to utilize information, and new methodologies to obtain information. For example, asking a user to enter a large amount of foodstuff information leads to low compliance. However, methods described herein enable easy entry of foodstuff information, resulting a better compliance and ability to utilize information.

Figure 7:
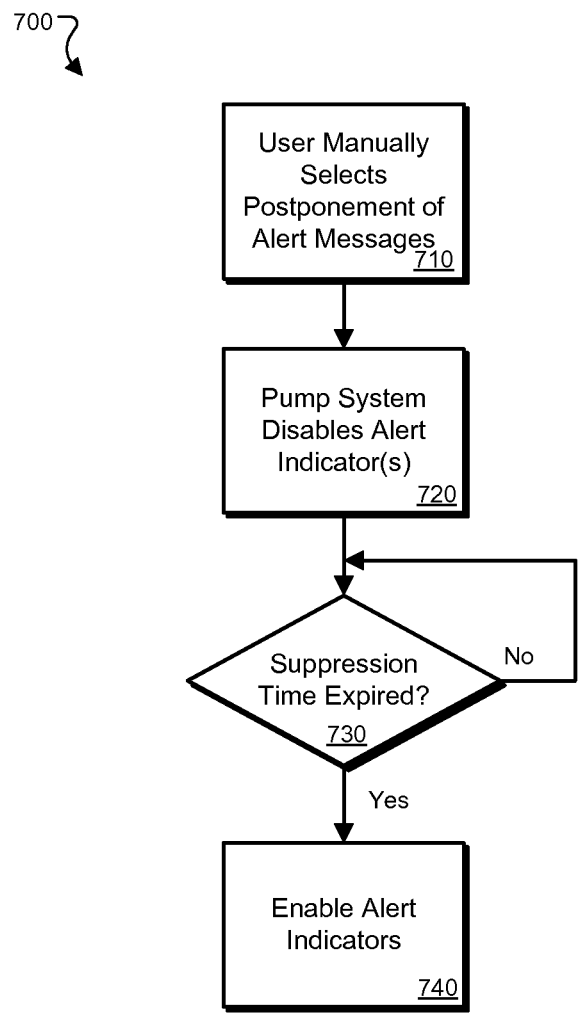
FIG. 7 is a flow chart illustrating a method of postponing alert messages in an infusion pump system.

FIG. 7 is a flow chart illustrating a method 700 of postponing disruptive alert messages in an infusion pump system.

The method 700 will be described in reference to an alert messaging system in an infusion pump. The alert messaging system may alert a pump user audibly, visually, or via another sense, such as a vibration (e.g., such that the user can feel an alarm is being generated). Visual indicators can include light emitting diodes (LEDs), touch screens, liquid crystal display (LCD) screens, or other visual devices. Audio indicators may include buzzer chips, piezoelectric indicators, or other technology, and the like. Thus, the alert messaging system can generate a disruptive alert to inform the user of an event.

In general, the alert messaging system may accept input from pump users, such as time, date and alarm or alert criteria. For example, the pump user may manually configure an alert-free period to suspend the receipt of the alerts for a set period of time (e.g. 4 hours). Alternatively, the pump user may manually request a suspension of the disruptive alerts until a certain specified time is reached (e.g. suspend until 6 am). As such, the pump may not produce or present audible, visual, or other disruptive alerts in that specified time period. In addition, the pump may be programmed to defer the alerts to either the resumption time or the end of time of the alert-free period.

The method 700 begins with the receipt 710 of a request for postponement of alert messages. For example, the pump user may enter a request for an alert-free period, or the system may activate a previously set alarm. Alert-free periods and alarms may be manually set by the pump user at any time. For example, preemptive alerts may be set in the pump system and may automatically engage at a set time.

When the alert postponement period begins, the infusion pump may disable 720 one or more indicators for the suspended alert. In some implementations, certain types of disruptive alerts may be suspended and replaced by other alert types. In one embodiment, the alert messaging system may replace audible or visual indicators with a vibration indicator, so that the pump will vibrate to provide an alert. As another example, a pump user may wish to suppress audio indicators for a long period of time, such as, during a seminar or meeting. Thus, the user may temporarily suspend audio alert indicators, but may still receive visual messaging and indicators.

In other implementations, all disruptive alerts may be suspended until a set time. The period of time may be determined by a requested period of time or may be determined by the period of time until the requested resumption time.

The method 700 may make inquiries over time to determine 730 whether or not the alert suppression time has expired. If the time has not completed, the suppression remains in progress and the system awaits expiration of the suppression time. If, however, the suppression time has expired, the alert indicators may be enabled 740 and the system may function accordingly. In addition to suspending alert messages, the pump system may also receive instructions to suspend other processes.

In some implementations, a health alert or alarm system may remain active even while the disruptive alert system has been disabled. Disruptive alerts generally relate to events, such as dispensing a bolus amount, a programmed change in infusion amounts, a reminder to check blood glucose levels, etc. Health alerts generally relate to health-critical events, which may have a significant health impact on the user if not addressed. Examples of events that may generate a health alerts include the container of medicine in the infusion pump reaching a low level, the container of medicine in the infusion pump being empty, a sensed blockage of flow from the infusion pump, or other events. As these events have a high priority, a health alert or alarm system may remain functional even during a requested alert suspension period.

As various pump devices may be bodily worn, and are typically very close to the user in many cases, the alert system used by the pump devices may be very disruptive and irritating. These disruptive alerts generally inform the user that a dosage has occurred, that a requested bolus was delivered, or other event. In many cases the user may already know that the event will be occurring. The advantages of disabling a disruptive alert system includes the advantages of turning off such alerts during meetings, during rest periods, or during periods requiring enhanced concentration. This enables the user (and others) to perform at an optimal level without distraction for a requested period. After the requested period, the pump system will automatically return to normal operation. Thus, no additional input or request is needed to return to normal operation. In addition, however, other types of alarms may be very important to the user, such as health alerts, that inform the user of a critical failure, problem, or other issue. These alarms may remain enabled even during the requested period for disabling disruptive alerts. This provides additional assurance and peace of mind to the user that critical alarms will not be missed.

Figure 8:
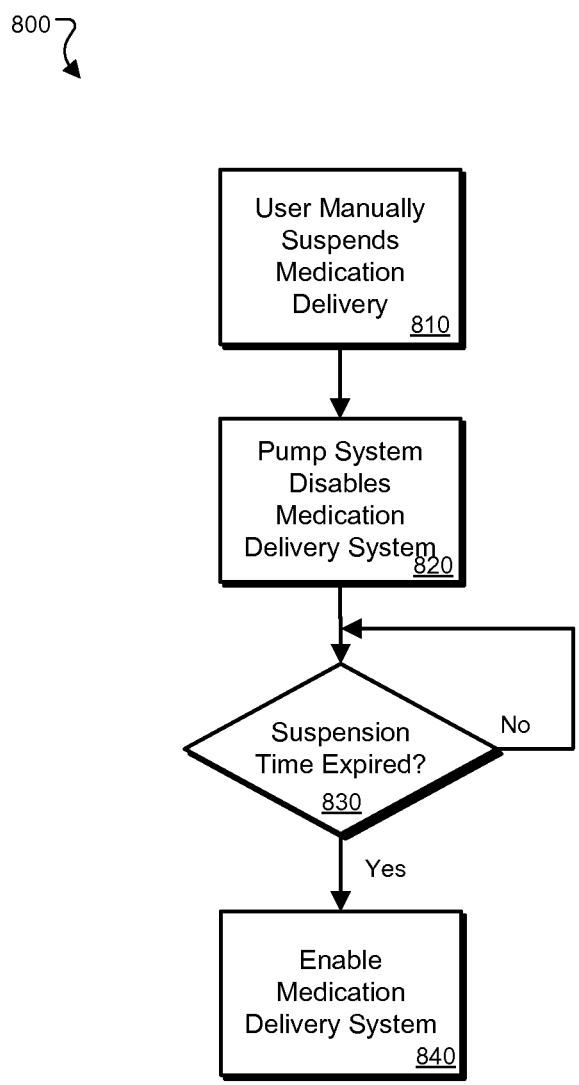
FIG. 8 is a flow chart illustrating a method of postponing medication dispersion in an infusion pump system.

FIG. 8 is a flow chart illustrating a method 800 of postponing medication dispersion in an infusion pump system.

The infusion pump may be equipped with a feature whereby the delivery of medication may be suspended temporarily at a specified time. The method 800 begins when the duration and time of suspension are entered 810 by the pump user, such as a patient or nurse, and the system can alert the user of the suspended status at a predetermined interval or period of time. The input can be manually entered into the infusion pump via a control center, graphical user interface, bar code reader, radio frequency (RF) reader, optical reader, infrared reader, wireless transmission via email or Internet, or other means suitable to enter data into a processing device.

Upon receiving a request to suspend medication, the system may disable 820 the medication delivery system. In some implementations, if suspended, the delivery of medication may be automatically or manually restarted after a predetermined period of time. In other implementations, the system may periodically assess 830 whether or not the entered suspension time has expired. If the suspension time has not expired, the system may continue to suspend medication and additional assessments may be performed in the future.

The medication delivery system may be enabled 840 for various reasons. In some implementations, expiration of the suspension time may invoke the pump system to enable the medication delivery system. In other implementations, a pump user may interrupt the medication delivery suspension to receive medications. For example, the pump user may be feeling symptoms that may require medication.

Figure 9:
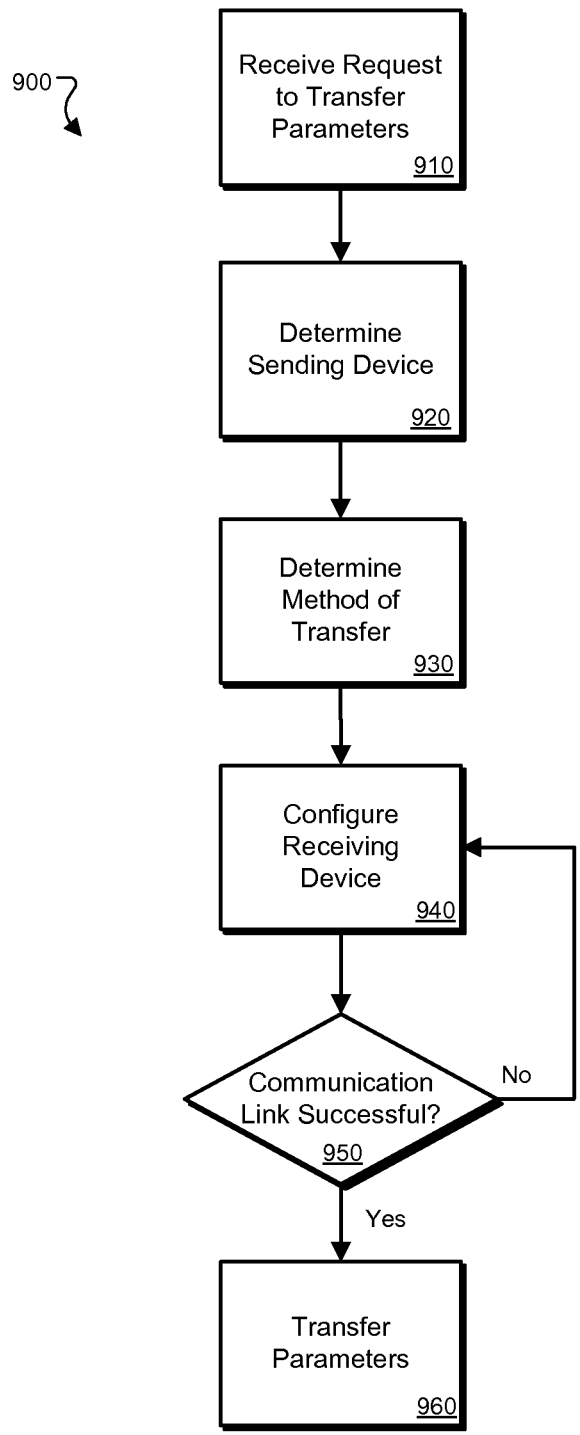
FIG. 9 is a flow chart illustrating a method of transferring infusion pump parameters to one or more devices.

FIG. 9 is a flow chart illustrating a method 900 of transferring infusion pump parameters to one or more devices.

At various times, the pump system may need to be replaced to ensure proper treatment of the user. For example, over time, the components in a pump may wear out and require replacing. In one embodiment, the pump system may include a mechanism portion, and a control portion that may be communicably coupled and uncoupled when either portion is replaced. In some implementations, the mechanism portion may be detachable and disposable, while the control portion remains intact. For example, an old pump mechanism may be replaced by a new pump mechanism. In other implementations, the entire pump system may be a single unit, with non-detachable mechanism and control portions. In some embodiments, the mechanism and control portions may be integrated.

The method of autonomous control may be initiated for a new or previously unused pump by the transfer of parameters from a current pump system to initiate proper operation. The program and information may be the entire set of parameters including, but not limited to, bolus profile, basal rate, real time clock ("RTC"), blood glucose history, delivery history, and bolus history. The transfer of parameters may be accomplished by transfer from an active or previously programmed unit or a separate programming device to a new, unused or unprogrammed unit. Parameters can be transferred to the new pump by either wired or wireless communications.

The method 900 begins when the infusion pump system receives 910 a request to transfer parameters. In particular, a pump user may manually enter a request to upload or download pump operating parameters or feedback of suggested manual parameters to a database, another pump, the Internet, or various computer programs or computer files, to name a few examples. In some implementations, the data to be transferred can be stored internally or externally before a transfer is performed.

In some implementations, the method of autonomous control may be initiated for a new or previously unused pump by the automatic transfer of parameters by which the pump may initiate proper operation. Such operating parameters may include, but are not limited to, bolus profile, basal rate, RTC, BG history, delivery history, and bolus history. In one embodiment, the transfer of parameters may be accomplished by transfer from an active or previously programmed unit to a new, unused or unprogrammed unit. In another embodiment, the transfer of parameters may be downloaded to a database and uploaded to the unprogrammed unit at another time. Alternatively, a new or unprogrammed pump may have the program and information loaded from a separate programming device. The separate programming device may be connected to an external computer or device with an interface that may run on graphical user interface (GUI) standards associated with that computer.

In general, when a transfer is requested, the pump user may determine 920 a sending device from which the parameters and feedback will be transferred. In one embodiment, the sending device may be the current pump device. In other embodiments, the sending device may be a database, a digital computing device such as a laptop, desktop, workstation, personal digital assistant, server, or another device communicably coupled to the system.

After determining the sending device, the user may determine 930 the method of transfer. This transfer may be initiated by means of direct, pump-to-pump physical contact, an infrared port, wireless connection, or by method and means of a wired connection, such as through a USB port, a serial port, or other technologies. The information transferred may provide a seamless transition between the "old" pump (sending device) and the "new" pump. Using a wired connection to transfer the parameters may facilitate communication by way of acoustic, electromagnetic, optical or other form of signaling. Ideally, the connection may be made and the transfer of information may be completed before the use of the pump. The transfer of parameters can also be accomplished using wireless communication between the pumps. In general, the wireless transfer of parameters or files can be sent from the sending device to a receiving device (e.g., a new infusion pump) through a wireless connection, such as Bluetooth, Ethernet, or wireless Ethernet, to name a few examples.

In the event that the transfer determined between two infusion pumps, the receiving device may be configured 940 appropriately to receive data. For example, memory on the device may be erased or configured to receive an upload of data, or other parameters, such as alert systems and displays may be tested for proper functionality. In addition, the communication link may be tested 950 to ensure proper bandwidth or sufficiency of streaming. The communication link may fail prior to or concurrently with the initiation of the transfer. In this example, one or more configuration programs may be performed again, in an attempt to repair the link.

Once the configuration is complete and the data is ready for transfer, the parameters may be transferred 960 to the new pump. Upon completion of the transfer, the pump user may manually enable other systems on the new pump, install medication supplies, or enter further data. In some implementations, the pump system may indicate, visually or audibly, that further action is required from the pump user. In some implementations, the new pump system may perform a system check routine to ensure the pump will properly operate.

Direct communication from pump to pump enables a user to transfer operating history, user information, configuration parameters, and other information directly form one unit to another. The advantages of such an approach may include the ability to make such a transfer without requiring any additional equipment or setup. An approach that requires, for example, uploading and downloading from an internet site requires an internet connection, access to the specific site, and additional equipment. The user may not have all of these elements when a pump unit begins to fail. Thus, pump to pump direct transfer enables the information to be captured in a new pump unit rather than lost in cases where the website is down for maintenance, the internet connection is slow or non-existent, or the user is on vacation or other location where additional equipment may not be present. Direct communication from pump nit to pump unit also enables the use of disposable pump units, while still retaining information and history. For example, direct pump information transfer may transfer identification, configuration, and user information, resulting in an easy and direct initialization of a second pump unit. In addition, operating history, historical dosage and consumption information may be transferred directly to a new pump unit. Thus, the user may completely replace the equipment used, but have the full information available in the new unit. Such an approach is not useful, and in fact, cannot be done where a pump unit is "dumb", and contains no processing or memory storage. Rather than using a separate control unit for all functions, and a pump unit for just dosing, a "smart" pump unit enables the use and transfer of information from the pump unit itself. Incorporating processing and memory capacity into the pump unit enables the use and transfer of additional information from one pump unit to another.

Figure 10:
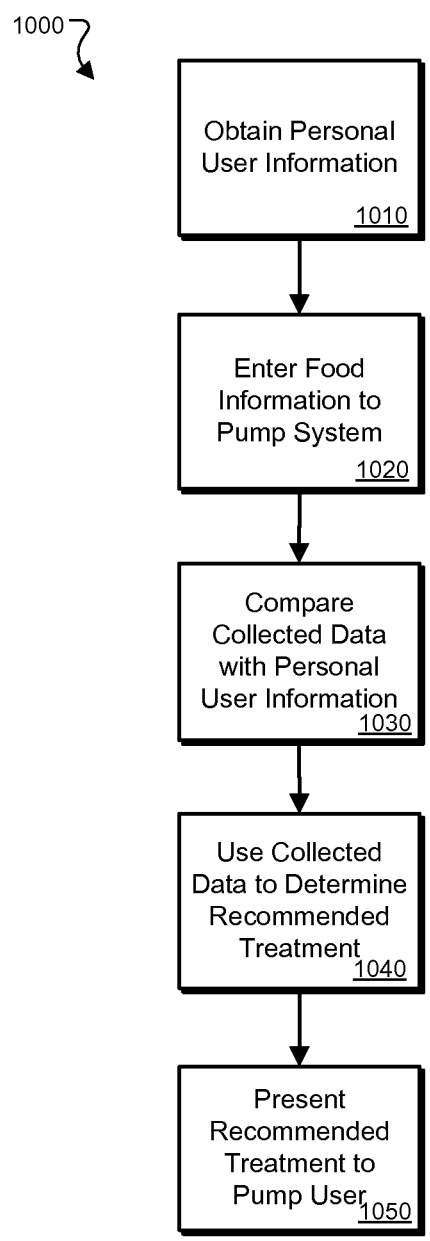
FIG. 10 is a flow chart illustrating a method for entering food data into an infusion pump to receive a treatment recommendation.

FIG. 10 is a flow chart illustrating a method 1000 for entering food data into an infusion pump to receive a treatment recommendation.

The method 1000 begins when personal user information is obtained 1010 from the user, or alternatively, accessed from the pump system. The pump user may manually enter personal information such as weight, medication ingested, exercise performed, or other health characteristics, and the system will store that data until needed in system analysis, for example. In some implementations, the personal user information can be used for analysis in determining recommended treatments or other suggestions for the pump user.

Next, the user may enter 1020 food information pertaining to food ingested for the day, or food about to be ingested. For example, the user may wish to know how much of a specific food item can be ingested without requiring medication. In another example, the user may simply wish to view statistics regarding prior consumption of the entered food.

In one example, the entered data may be analyzed, or compared 1030 with personal user information to determine proper bolus amounts and rates. For example, from the analyzed data, the system may internally determine the parameters for FOB and recommended bolus amount such as the example described in FIG. 3 above. In some implementations, the comparison 1030 may be performed to increase or decrease a medication dosage. For example, if the pump user has ingested a particularly high quantity of sugar filled food in one day, an analysis may be performed to determine whether or not to increase the insulin dosage.

Thus, user entered data may be used to determine 1040 any number of recommended treatments to benefit the health of the pump user. Recommended treatments may include medication dosages, consultant notices (e.g., consult a physician), technical support (e.g., to repair the pump for some reason), or simply recommendations on food consumption (e.g., dietary recommendations) and the like. Other treatment recommendations are possible in the system.

Some, all, or none of the determined treatments may be presented 1050 to the pump user in the user interface of the pump device. The pump user may accept, modify, or decline a proposed treatment. As such, treatment recommendations may typically await user feedback before carrying out the actual treatment. In some implementations, the recommended treatment may require a doctor's visit. In other implementations, the pump system may carry out the recommended treatment after the user accepts the treatment.

The user may also enter other types of input into the system. In one embodiment, device-assisted data entry may be used to enter foodstuff information. Typically, a user may be willing to enter carbohydrate information related to the food consumed. However, requesting additional information generally results in poor compliance. Using device-assisted data entry provides a method of obtaining additional foodstuff information that may be useful in determining recommended treatment amounts of a medicine or other material. Examples of device-assisted data entry include the use of barcode information, RFID tags, or food codes. The information may enter the pump system via various communication interfaces, such as those shown in the example embodiment of FIGS. 1-3.

In some embodiments, the data entered may include foodstuff information directly, such as amount of calories, carbohydrates, fats, and proteins. In most embodiments, however, the data entered may be used as a key or code by the system to obtain additional foodstuff information. For example, a database having various food values (including carbohydrate, fat, and protein content), and their typical amounts may be downloaded to the pump system. The database can be used to compare typical "servings" of food items against what a user may consume. The device-assisted data entry may enter a code value, which is then looked up in the database by the system to obtain various food values. The database may be provided as part of the pump system, may be uploaded wirelessly from the Internet, and/or may require further user interaction to appropriately store and use the database in the pump system. As such, an onboard assistance device may assist 524 the user in walking through configuration steps to ensure the database operates properly. The onboard assistance device may also intervene to assist the user for other unknown data entries.

The advantages of such an approach include the ability to utilize additional foodstuff information for the treatment of the user. Importantly, the additional foodstuff information may be obtained without requiring numerous additional steps or tasks by the user, and in some cases may require less input from a user. Thus, an approach that includes additional foodstuff information, enabling better treatment, may be easier for the user. As device assisted data entry may be easier, this approach may also increase user compliance with entering food and consumption information.

Figure 12:
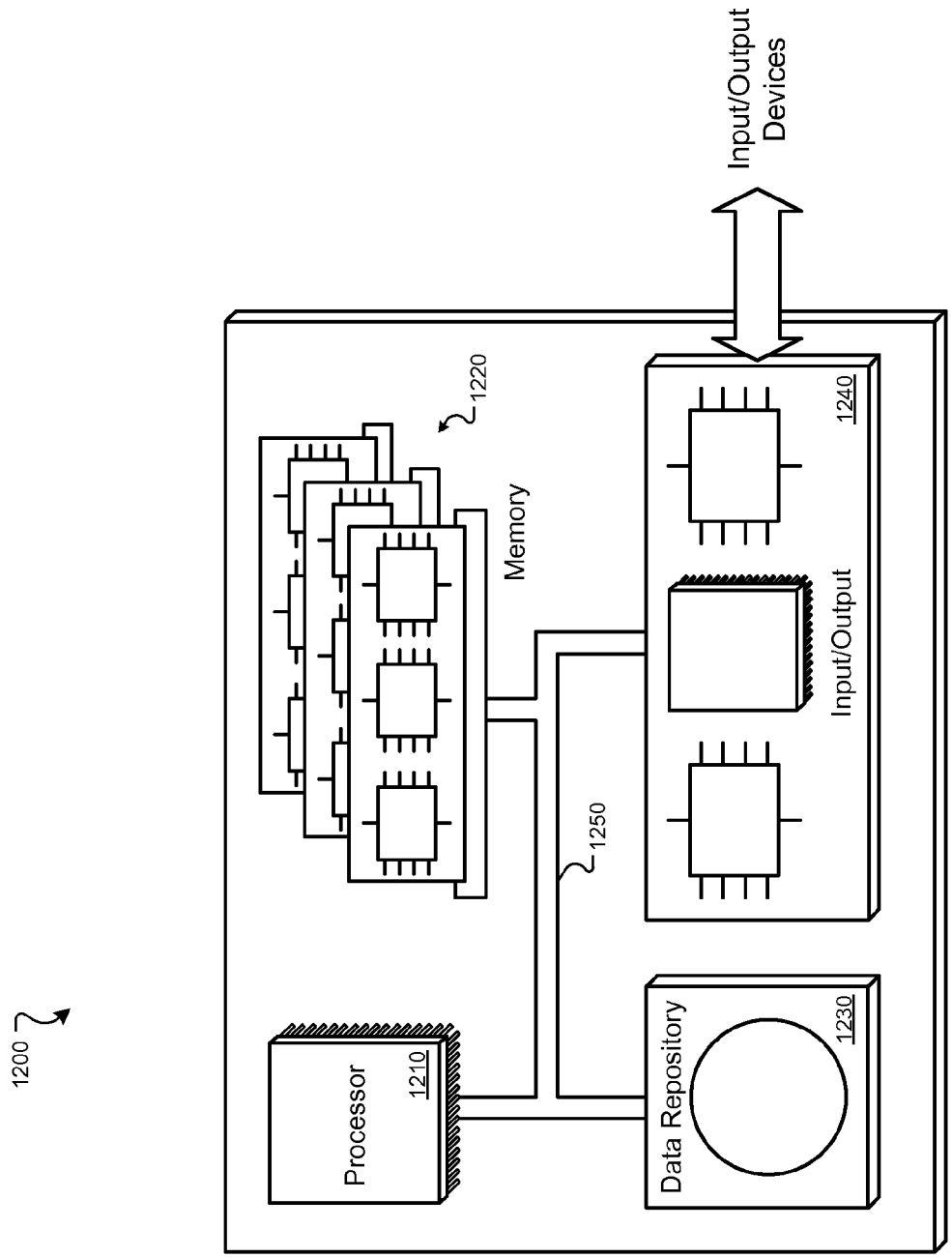
FIG. 12 is a schematic diagram of an example of a generic infusion pump computing system.

In some implementations, the methods 400-1000 may be performed by processing devices, such as those shown in FIG. 12 of this description. The processing devices may be located in a control unit, in the pump body, or in some combination thereof. In particular, when processing equipment is used by one of the above methods, the system may select one or more devices, from the system in FIG. 12 or another system, to perform the operations in the methods. In addition, the input received in the system, or as part of the above operations may be received in a user interface, such as through a touch screen, keyboard, or other manual entry device, a data collection device, such as can be connected to interfaces 212, 214, or 216.

Figure 11:
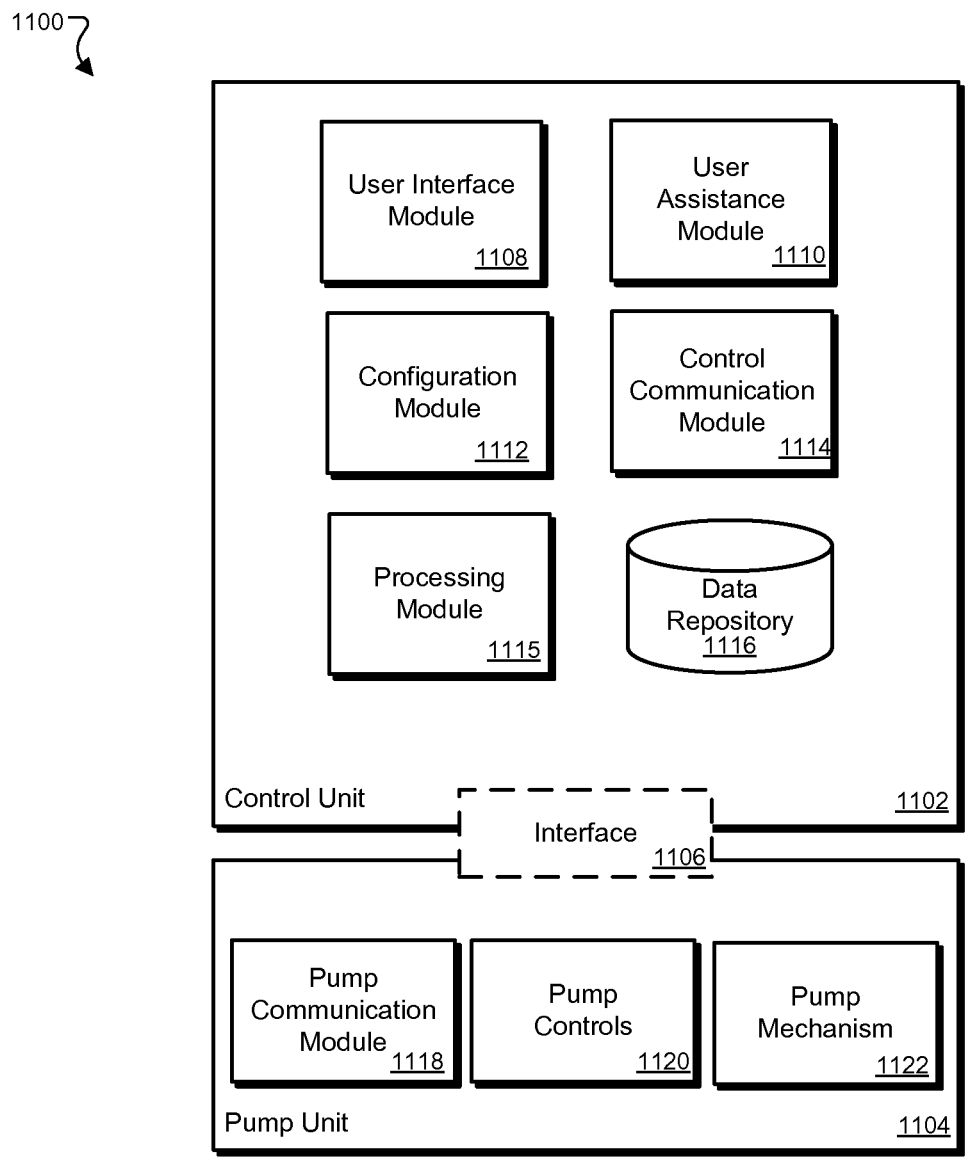
FIG. 11 is a block diagram illustrating an exemplary architecture for operating and controlling an infusion pump system.

Several systems may be used to carry out the operations in the methods described above. As such, FIG. 11 is simply one exemplary system for performing the operations in FIGS. 4-10. Accordingly, the above description of example embodiments does not define or constrain this disclosure to a particular system. Other changes, substitutions, and alterations are also possible without departing from the spirit and scope of this disclosure.

FIG. 11 is a block diagram illustrating an exemplary architecture 1100 for operating and controlling an infusion pump system. For example, the architecture 1100 may receive user instructions in one or more communication interfaces, such as the infrared port 212, USB port 214, RFID reader 216, or another attached interface, and may then implement the user instructions accordingly. In some implementations, the architecture may respond to user instructions or requests with inquiries about the user entered instructions. For example, if a foodstuff is received via the RFID reader 216, the architecture 1100 may respond to request a particular mass for the entered foodstuff.

The architecture 1100 includes a control unit 1102 and a pump unit 1104 that may be communicably coupled through interface 1106. The interface 1106 facilitates wireless, wired, contact, near proximity, or contactless communication between the control unit 1102 and the pump unit 1104. While illustrated as a single or continuous interface, the interface 1106 may be logically divided into individual interfaces on either unit 1102 or 1104 without departing from the scope of this disclosure, so long as at least a portion of the interface 1106 may facilitate communications between the control unit 1102 and the pump unit 1104.

The control unit 1102 may include various modules to perform functions in the pump system. The modules may include a user interface module 1108, a user assistance module 1110, a configuration module 1112, a control communication module 1114, and a processing module 1115. The modules may interact with the pump user, the pump unit 1104, and other system components, as necessary to carry out system tasks. For example, the modules may control the dispensing of medication by controlling the reservoir 105. The modules may be stored in a nonvolatile storage location, such as data repository 1116 or another repository in the system, and may be transferred to memory 1116 for active use by the architecture 1100.

The user interface module 1108 may provide the user with a mechanism to input data into the pump system. Here, the user interface module 1108 may also display system information to the pump user, such as BG history or recommended bolus information, for example.

The user assistance module 1110 may provide guidance and recommendations to the user when a system function is scheduled, or when the user has requested a system modification. In some implementations, the user assistance module 1110 may provide suggestions and calculation values to assist the user in determining a course of action for the pump system.

The configuration module 1112 may configure the pump system upon user request. For example, pump components, such as the drive mechanism 202 can be configured to the pump system parameters upon receiving a request from the pump user. In addition, the configuration module 1112 may configure a new pump upon installation. In general, the configuration module 1112 may be user controlled, and thus, may not have prior system settings. For example, pump users may input personal information to "calibrate" the configuration module 1112 to appropriate settings.

The control communication module 1114 may receive user information via the user interface module 1108, a barcode reader, an RF reader, a PDA, a cell phone, or other such technology, and transfer the data to the pump unit 1104. For example, the control communication module 1114 may transfer user entered data, calculation data, modification data, operating instructions, and the like to the pump unit 1104. The pump unit 1104 may then carry out any instructions, or user modifications that the control unit 1102 deemed necessary.

The processing module 1115 may include one or more processors to execute instructions and manipulate data for performing the operations of the control unit 1104. The processing module 1115 may include a central processing unit (CPU), an application specific integrated circuit (ASIC), a field-programmable gate array (FPGA), or other suitable hardware or software control system, for example.

The control unit 1102 may include local electronic storage capacity, such as data repository 1116. The data repository 1116 may include any memory or database module and may take the form of volatile or non-volatile memory including, without limitation, magnetic media, optical media, random access memory (RAM), read-only memory (ROM), removable media, or any other suitable local or remote memory component. The illustrated data repository 1116 may store system data, such as alert data, food data, medication data, reporting files, system parameters, user entered data, and others.

The pump unit 1104 may include a pump communication module 1118, pump controls 1120, and a pump mechanism 1122. In general, the pump communication module 1118 may receive instructions from the control communication module 1114. Specifically, user instructions or requests may be entered into the user interface module 1108 of the control unit 1102, whereby, the control communication module 1114 may transfer the instructions or requests into the pump communication module 1118. The module 1118 may then provide the information to the pump controls 1120 which may translate the instructions for the pump mechanism 1122.

The pump controls 1120 may include one or more processors to execute instructions and manipulate data for performing the operations of the pump unit 1104. The pump controls 1120 may include, for example, CPUs, ASICs, FPGAs, or other suitable hardware or software control system. In the illustrated implementation, the pump controls 1120 translate instructions for the pump mechanism 1122. The pump mechanism 1122 may deliver medication dosages to the pump user. For example, the pump mechanism 1122 can deliver a medication such as insulin in a basal dose, or a bolus dose to correct BG levels in the pump user's body.

In some implementations, the control unit 1102 may be included as a portion of the pump unit 1104. In other implementations, the control unit 1102 may be a separate, detachable entity from the pump unit 1104. Regardless of whether or not the control unit 1102 and the pump unit 1104 are separate entities, in operation, system processing may occur in the control unit 1102, in the pump unit 1104, or may occur in a combination of both.

FIG. 12 is a schematic diagram of an example of a generic infusion pump computing system 1200. The system 1200 can be used for the operations described in association with the methods in this disclosure according to one implementation. For example, the system 1200 may be included in any or all of the computing system 800, the pumps 900, 1000 or 1100.

The system 1200 includes a processor 1210, a memory 1220, a storage device 1230, and an input/output device 1240. Each of the components 1210, 1220, 1230, and 1240 are interconnected using a system bus 1250. The processor 1210 is capable of processing instructions for execution within the system 1200. In one implementation, the processor 1210 is a single-threaded processor. In another implementation, the processor 1210 is a multi-threaded processor. The processor 1210 is capable of processing instructions stored in the memory 1220 or on the storage device 1230 to display graphical information for a user interface on the input/output device 1240. The processors shown in FIG. 12 may be included in some, all, or none of the modules shown in FIG. 11. The processors and modules may be located within a pump body (such as the example pump body shown in FIGS. 1-3), or may be located within a control unit. In some embodiments, the control unit may be detachable from the pump body. In some embodiments, some of the modules or processors may be located in a control unit, while others are located within a pump body.

The memory 1220 stores information within the system 1200. In one implementation, the memory 1220 is a computer-readable medium. In one implementation, the memory 1220 is a volatile memory unit. In another implementation, the memory 1220 is a non-volatile memory unit.

The storage device 1230 is capable of providing mass storage for the system 1200. In one implementation, the storage device 1230 is a computer-readable medium. In various different implementations, the storage device 1230 may be a floppy disk device, a hard disk device, an optical disk device, or a tape device.

The input/output device 1240 provides input/output operations for the system 1200. In one implementation, the input/output device 1240 includes a keyboard and/or pointing device. In another implementation, the input/output device 1240 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device or in a propagated signal, for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computing system will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of nonvolatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computing device or infusion pump device having a display device an LCD (liquid crystal display) monitor for displaying information to the user and a keyboard, keypad, or pointing device by which the user can provide input to the computer.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations, one or more features from a claimed combination can in some cases be excised from the combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Although the present invention has been described with reference to specific embodiments, these embodiments are illustrative only and not limiting. Many other applications and embodiments of the present invention will be apparent in light of this disclosure and the following claims.

What is claimed is:

1. A method of entering food information into a pump unit of an infusion pump system, comprising:
providing a foodstuff identification; and
using device-assisted data entry to enter the foodstuff identification into a pump unit of an infusion pump system via a foodstuff data input device contained within the pump unit, wherein the foodstuff data input device provides said device-assisted data entry of said foodstuff identification;
wherein the infusion pump system is configured to use the entered foodstuff identification to retrieve foodstuff composition information from an onboard data repository of the pump unit.

2. The method of claim 1, wherein the foodstuff identification comprises a radio frequency identification (RFID) tag.

3. The method of claim 1, wherein the foodstuff identification is entered using a radio frequency identification (RFID) reader in an infusion pump system.

4. The method of claim 1, wherein the foodstuff identification comprises a universal product code (UPC) barcode.

5. The method of claim 1, wherein the foodstuff identification is entered using a scanner in an infusion pump system.

6. The method of claim 1, wherein the infusion pump system is configured to determine a recommended bolus amount based at least partially on the foodstuff composition information.

7. The method of claim 6, wherein the foodstuff composition information retrieved by the infusion pump system includes carbohydrate, fat, and protein composition information of a foodstuff.

8. The method of claim 6, wherein the infusion pump system is configured to determine said recommended bolus amount based at least partially on user metabolism information.

9. The method of claim 6, wherein the infusion pump system is configured to determine said recommended bolus amount based at least partially on a user's food on board and insulin on board information.

10. The method of claim 6, wherein the infusion pump system is configured to determine said recommended bolus amount based the following equation:

$$\text{Recommended bolus amount} = \text{Food Now} * \text{Carb Ratio} + (BG - BG_{target}) * \text{insulin sensitivity} - IOB + FOB,$$

where: IOB=insulin on board;
FOB=food on board;
Food Now=the amount and type of foodstuffs ingested expressed in terms of grams of: carbohydrates, proteins or fat;
BG=blood glucose level; and
BGtarget=target blood glucose level.

11. A method of entering food information into an infusion pump system, comprising:
providing a foodstuff identification; and
using device-assisted data entry to enter the foodstuff identification into an infusion pump system;
wherein the infusion pump system comprises a foodstuff data input device wholly contained by a pump body of the infusion pump system, the foodstuff data input device configured to provide said device-assisted data entry of said foodstuff identification, and
wherein the infusion pump system comprises: the pump body; a medicine reservoir insertable into an interior space of the pump body through an opening in the pump body; a drive system positioned in the pump body; and a control system configured to communicate with the foodstuff data input device.

12. The method of claim 11, wherein the foodstuff data input device comprises a radio frequency identification (RFID) reader connected to the control system of the infusion pump system.

13. The method of claim 11, wherein the foodstuff data input device comprises a scanner connected to the control system of the infusion pump system.

14. The method of claim 11, wherein the foodstuff identification comprises a radio frequency identification (RFID) tag, and wherein the foodstuff identification is entered using a radio frequency identification (RFID) reader contained within the pump body.

15. The method of claim 11, wherein the foodstuff identification comprises a universal product code (UPC) barcode, and wherein the foodstuff identification is entered using a scanner contained within the pump body.

16. The method of claim 11, wherein the infusion pump system is configured to use the entered foodstuff identification to retrieve foodstuff composition information from an onboard data repository stored on a memory device contained within the pump body, and wherein the infusion pump system is configured to determine a recommended bolus amount based at least partially on the foodstuff composition information.

* * * * *